US009700534B2

(12) United States Patent
Freeman et al.

(10) Patent No.: US 9,700,534 B2
(45) Date of Patent: *Jul. 11, 2017

(54) NITRATED-FATTY ACIDS MODULATION OF TYPE II DIABETES

(71) Applicant: University of Pittsburgh—of the Commonwealth System of Higher Education, Pittsburgh, PA (US)

(72) Inventors: Bruce A. Freeman, Pittsburgh, PA (US); Francisco J. Schopfer, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/923,265

(22) Filed: Oct. 26, 2015

(65) Prior Publication Data
US 2016/0045467 A1 Feb. 18, 2016

Related U.S. Application Data

(63) Continuation of application No. 14/244,741, filed on Apr. 3, 2014, now Pat. No. 9,186,408, which is a continuation of application No. 13/666,827, filed on Nov. 1, 2012, now Pat. No. 8,735,449, which is a continuation of application No. 12/670,951, filed as application No. PCT/US2008/009274 on Aug. 1, 2008, now Pat. No. 8,324,277.

(60) Provisional application No. 60/953,360, filed on Aug. 1, 2007.

(51) Int. Cl.
*A61K 31/20* (2006.01)
*A61K 31/201* (2006.01)
*A61K 45/06* (2006.01)

(52) U.S. Cl.
CPC ............ *A61K 31/201* (2013.01); *A61K 31/20* (2013.01); *A61K 45/06* (2013.01)

(58) Field of Classification Search
CPC .................................................... A61K 31/20
USPC ........................................................ 514/560
See application file for complete search history.

(56) References Cited

U.S. PATENT DOCUMENTS

| | | | |
|---|---|---|---|
| 3,578,687 A | 5/1971 | Larkin et al. | |
| 3,819,561 A | 6/1974 | Bruenner | |
| 3,917,660 A | 11/1975 | Sasaki et al. | |
| 4,599,430 A | 7/1986 | Milberger et al. | |
| 5,412,137 A | 5/1995 | Prashad et al. | |
| 5,741,211 A | 4/1998 | Renirie et al. | |
| 6,187,747 B1 | 2/2001 | Singh et al. | |
| 6,262,029 B1 | 7/2001 | Press et al. | |
| 6,346,231 B1 | 2/2002 | Opheim | |
| 6,376,688 B1 | 4/2002 | Ferrante et al. | |
| 6,407,075 B1 | 6/2002 | Scott et al. | |
| 6,410,802 B1 | 6/2002 | Dasseux et al. | |
| 6,531,150 B1 | 3/2003 | Sunohara et al. | |
| 6,652,879 B2 | 11/2003 | Opheim | |
| 6,924,309 B2 | 8/2005 | Ferrante et al. | |
| 6,998,395 B2 | 2/2006 | Jackson et al. | |
| 7,312,191 B2 | 12/2007 | Rose et al. | |
| 7,452,907 B2 | 11/2008 | Cheng et al. | |
| 7,776,916 B2 | 8/2010 | Freeman et al. | |
| 7,977,315 B2 | 7/2011 | Rose et al. | |
| 8,309,526 B2 | 11/2012 | Freeman et al. | |
| 8,324,277 B2 | 12/2012 | Freeman | |
| 8,563,609 B2 | 10/2013 | Miller | |
| 8,686,038 B2 | 4/2014 | Yang | |
| 8,686,167 B2 | 4/2014 | Miller | |
| 8,735,449 B2 * | 5/2014 | Freeman | A61K 31/201 514/560 |
| 8,933,255 B2 | 1/2015 | Miller | |
| 8,937,194 B2 | 1/2015 | Miller | |
| 9,006,473 B2 | 4/2015 | Freeman et al. | |
| 9,066,902 B2 | 6/2015 | Freeman et al. | |
| 9,186,408 B2 | 11/2015 | Freeman et al. | |
| 9,192,600 B2 | 11/2015 | Yang | |
| 9,271,952 B2 | 3/2016 | Cushing | |
| 9,295,678 B2 | 3/2016 | Freeman et al. | |
| 9,308,189 B2 | 4/2016 | Miller | |
| 2001/0037598 A1 | 11/2001 | Suppes et al. | |
| 2002/0128510 A1 | 9/2002 | Durley et al. | |
| 2003/0078299 A1 | 4/2003 | Ferrante et al. | |
| 2004/0006248 A1 | 1/2004 | Paiocchi et al. | |

(Continued)

FOREIGN PATENT DOCUMENTS

| | | |
|---|---|---|
| EP | 1407767 A1 | 4/2004 |
| EP | 1772149 A1 | 4/2007 |

(Continued)

OTHER PUBLICATIONS

Baker et al., "Fatty Acid Transduction of Nitric Oxide Signaling," *The Journal of Biological Chemistry*, 280(51):42464-42475, Dec. 23, 2005.

Kim et al., "The effect of PPAR-γ agonist on glucose metabolism and insulin sensitivity in on-obese type 2 diabetic rat models," *Diabetes, American Diabetes Association* 55: Suppl. 1, Jun. 1, 2006.

Marx et al., "Peroxisome Proliferator-Activated Receptors and Atherogenesis: Regulators of Gene Expression in Vascular Cells," *Circulation Research*, 94(9):1168-1178, May 14, 2004.

Mitschke et al., "9- and 10-Nitro-oleic acid do not interfere with the GC-MS quantitative determination of nitrate and nitrate in biological fluids when measured as their pentafluorobenzyl derivatives," *Journal of Chromatography*, 85(1):287-291, May 2007.

(Continued)

*Primary Examiner* — Raymond Henley, III
(74) *Attorney, Agent, or Firm* — Klarquist Sparkman, LLP

(57) ABSTRACT

Nitro oleic acid and related metabolites are agonists of PPAR-γ. Surprisingly, nitro oleic acid is a more potent agonist of PPAR-γ, relative to nitro linoleic acid. Thus, nitro oleic acid and its metabolites, as well as their pharmaceutically acceptable salts and prodrug forms, are candidate therapeutics for the treatment of type-2 diabetes, which results from insulin resistance accompanying the improper functioning of PPAR-γ.

12 Claims, 6 Drawing Sheets

(56) References Cited

U.S. PATENT DOCUMENTS

| | | |
|---|---|---|
| 2004/0092590 A1 | 5/2004 | Arterburn et al. |
| 2004/0147599 A1 | 7/2004 | Gagnon et al. |
| 2004/0176451 A1 | 9/2004 | Tamai et al. |
| 2004/0254240 A1 | 12/2004 | Ferrante et al. |
| 2005/0136103 A1 | 6/2005 | Ben-Sasson et al. |
| 2005/0232981 A1 | 10/2005 | Ben-Sasson |
| 2006/0018874 A1 | 1/2006 | Radhakrishnan et al. |
| 2006/0063953 A1 | 3/2006 | Maurizio et al. |
| 2006/0100278 A1 | 5/2006 | Cooper et al. |
| 2006/0241088 A1 | 10/2006 | Arterburn et al. |
| 2007/0232579 A1 | 10/2007 | Freeman et al. |
| 2007/0275893 A1 | 11/2007 | Quay |
| 2008/0096961 A1 | 4/2008 | Serhan et al. |
| 2009/0326070 A1 | 12/2009 | Freeman et al. |
| 2010/0166918 A1 | 7/2010 | Miller |
| 2010/0216884 A1 | 8/2010 | Freeman |
| 2010/0286257 A1 | 11/2010 | Perricone |
| 2010/0286271 A1 | 11/2010 | Perricone |
| 2010/0286272 A1 | 11/2010 | Perricone |
| 2010/0331268 A1 | 12/2010 | Freeman et al. |
| 2011/0082206 A1 | 4/2011 | Miller |
| 2011/0092654 A1 | 4/2011 | Yang |
| 2011/0196037 A1 | 8/2011 | Yang |
| 2011/0319325 A1 | 12/2011 | Miller |
| 2012/0136034 A1 | 5/2012 | Freeman et al. |
| 2013/0059912 A1 | 3/2013 | Freeman |
| 2013/0101514 A1 | 4/2013 | Cushing |
| 2013/0210917 A1 | 8/2013 | Freeman et al. |
| 2014/0024713 A1 | 1/2014 | Yang |
| 2014/0243380 A1 | 8/2014 | Yang |
| 2015/0018417 A1 | 1/2015 | Freeman et al. |
| 2015/0051283 A1 | 2/2015 | Dighiero et al. |
| 2015/0246059 A1 | 9/2015 | Freeman et al. |
| 2016/0081961 A1 | 3/2016 | Cushing |
| 2016/0151318 A1 | 6/2016 | Yang |
| 2016/0151391 A1 | 6/2016 | Freeman et al. |

FOREIGN PATENT DOCUMENTS

| | | |
|---|---|---|
| GB | 587992 | 5/1947 |
| GB | 1407932 | 10/1975 |
| JP | 62-132804 | 6/1987 |
| WO | WO 98/09621 A | 3/1998 |
| WO | WO 01/06983 A2 | 2/2001 |
| WO | WO 01/15673 A3 | 3/2001 |
| WO | WO 01/21575 A1 | 3/2001 |
| WO | WO 01/60778 A2 | 8/2001 |
| WO | WO 01/78654 A2 | 10/2001 |
| WO | WO 01/78719 A1 | 10/2001 |
| WO | WO 01/79156 A1 | 10/2001 |
| WO | WO 02/22559 A2 | 3/2002 |
| WO | WO 02/102364 A1 | 12/2002 |
| WO | WO 03/031399 A1 | 4/2003 |
| WO | WO 03/039533 A1 | 5/2003 |
| WO | WO 2005/073164 A1 | 8/2005 |
| WO | WO 2005/110396 A2 | 11/2005 |
| WO | WO 2006/055965 A2 | 5/2006 |
| WO | WO 2006/086727 A2 | 8/2006 |
| WO | WO 2007/140433 A2 | 12/2007 |
| WO | WO 2008/008767 A2 | 1/2008 |
| WO | WO 2008/011085 A1 | 1/2008 |
| WO | WO 2008/103753 A2 | 8/2008 |
| WO | WO 2009/017802 A1 | 2/2009 |
| WO | WO 2009/038671 A2 | 3/2009 |
| WO | WO 2009/129495 A1 | 10/2009 |
| WO | WO 2009/134383 A2 | 11/2009 |
| WO | WO 2009/149496 A1 | 12/2009 |
| WO | WO 2009/155439 A2 | 12/2009 |
| WO | WO 2010/042877 A1 | 4/2010 |
| WO | WO 2010/078504 A1 | 7/2010 |
| WO | WO 2010/129763 A1 | 11/2010 |
| WO | WO 2010/129777 A1 | 11/2010 |
| WO | WO 2011/011882 A1 | 2/2011 |
| WO | WO 2011/014261 A1 | 2/2011 |
| WO | WO 2011/098746 A1 | 8/2011 |

OTHER PUBLICATIONS

Ryan et al., "Diabetes and the Mediterranean diet: a beneficial effect of oleic acid on insulin sensitivity, adipocyte glucose transport and endothelium-dependent vasoreactivity," *Q J Med*, 93:85-91, 2000.
Communication pursuant to Article 94(3) EPC for European Application No. 08 780 348.2-2123 dated Jul. 26, 2011.
International Search Report for International Application No. PCT/US08/09274 dated Oct. 24, 2008.
Supplementary European Search Report from European Application No. EP 08 78 0348 dated Jul. 30, 2010.
Summons to Attend Oral Proceedings dated Oct. 2, 2012, from corresponding European Patent Application No. 08780348.
Abud-Mendoza et al., "Treating severe systemic lupus erythematosus with rituximab. An open study," *Reumatol. Clin*. 2009, vol. 5, No. 4, 147-152.
Adjei et al., "A Phase I Trial of the Farnesyl Transferase Inhibitor SCH66336: Evidence for Biological and Clinical Activity," *Cancer Res*. Apr. 1, 2000, vol. 60, 1871-1877.
Akaike et al., "Antagonistic Action of Imidazolineoxyl N-Oxides against Endothelium-Dreived Relaxing Factor/*NO through a Radical Reaction," *Biochem*. 1993, vol. 32, 827-832.
Alber, "Signaling mechanisms of the *Mycobacterium tuberculosis* receptor Ser/Thr protein kinases," *Curr. Opin. Struct. Biol*. Dec. 2009, vol. 19, No. 6, 650-657.
Altschul et al., "Gapped BLAST and PSI-BLAST: a new generation of protein database search programs," *Nucleic Acids Res*. 1997, vol. 25, No. 17, 3389-3402.
Anand et al., "Synthesis and Evaluation of Small Libraries of Triazolylmethoxy Chalcones, Flavanones and 2-aminopyrimidines as Inhibitors of Mycobacterial FAS-II and PknG," *Bioorganic & Medicinal Chem*. 2012, vol. 20, No. 17, 5150-5183.
Arnold et al., "Nitric oxide activates guanylate cyclase and increases guanosine 3':5'-cyclic monophosphate levels in various tissue preparations," *Proc. Natl. Acad. Sci*. 1977. vol. 74, 3203-3207.
Artim et al., "Nitro-oleic acid targets transient receptor potential (TRP) channels in capsaicin sensitive afferent nerves of rat urinary bladder," *Expt. Neurol*. 2011, vol. 232, 90-99.
Asakura et al., "Synthesis and biological evaluation of γ-fluoro-β, γ-unsaturated acids," *J. of Flourine Chem*. 2006, vol. 127, 800-808.
Baker et al., "Red cell membrane and plasma linoleic acid nitration products: Synthesis, clinical identification, and quantitation," *Proc. Natl. Acad. Sci*. Aug. 10, 2004, vol. 101, No. 32, 11577-11582.
Baker et al., "Convergence of nitric oxide and lipid signaling: Anti-inflammatory nitro-fatty acids," *Free Radic. Biol. Med*. 2009, vol. 46, 989-1003.
Baker et al., "Nitro-fatty Acid Reaction with Glutathione and Cysteine; Kinetic Analysis of Thiol Alkylation by a Michael Addition Reaction," *J. of Biol. Chem*. Oct. 19, 2007, vol. 282, No. 42, 31085-31093.
Balazy et al., "Vicinal Nitrohydroxyeicosatrienoic Acids: Vasodilator Lipids Formed by Reaction of Nitrogen Dioxide with Arachidonic Acid," *J. Pharmacol. ExTher*. 2001, vol. 299, No. 2, 611-619.
Balazy, "Isomerization and Nitration of Arachidonic Acid by Nitrogen Dioxide," *Advances in Mass Spectrometry* 2001, vol. 15, 375-376.
Baldus et al., "Endothelial transcytosis of myeloperoxidase confers specificity to vascular ECM proteins as targets of tyrosine nitration," *J. Clin. Invest*. 2001, vol. 108, No. 12, 1759-1770.
Baldus et al., "Is NO News Bad News in Acute Respiratory Distress Syndrome," *Am. J. Respir. Crit. Care Med*. 2001, vol. 163, 308-310.
Ballini et al., "Nitroalkanes and Ethyl Glyoxalate as Common Precursors for the Preparation of both β-keto Esters and α,β-unsaturated Esters," *Tetrahedron Letters* 2004, vol. 45, 7027-7029.
Ballini et al., "Fast Diastereoselective Baylis-Hillman Reaction by Nitroalkenes: Synthesis of Di- and Triene Derivatives," *Tetrahedron* 2004, vol. 60, 4995-4999.
Ballini et al., "(Z)-7-Nitro-3-Heptene as Central Intermediate for the Synthesis of Jasmone, Methyl Jasmonate and γ-Jasmolactone," *Synthetic Communications* 1989, vol. 19, Nos. 3-4, 575-583.
Banker et al., *Modern Pharmaceutics*, Marcel Dekker, Inc. 1979, New York (TOC).

(56) References Cited

OTHER PUBLICATIONS

Bates et al., "Nitroalkene Fatty Acids Mediate Activation of Nrf2/ARE-Dependent and PPARγ-Dependent Transcription by Distinct Signaling Pathways and with Significantly Different Potencies," *Biochem.* 2011, vol. 50, 7765-7773.
Bates et al., "Noncatalytic Interactions between Glutathione S-Transferases and Nitroalkene Fatty Acids Modulate Nitroalkene-Mediated Activation of Peroxisomal Proliferator-Activated Receptor γ," *Biochem.* 2009, vol. 48, 4159-4169.
Batthyany et al., "Reversible Post-translational Modification of Proteins by Nitrated Fatty Acids In Vivo," *J. Biol. Chem.* Jul. 21, 2006, vol. 281, No. 29, 20450-20463.
Baumer, "Iodostarin 'Roche' in the treatment of Syphilis," *Deutsche Medizinische Wochenschrift* 1913, vol. 39, 1361 (case abstract) (1 page).
Beckman et al., "Apparent hydroxyl radical production by peroxynitrite: Implications for endothelial injury from nitric oxide and superoxide," *Proc. Natl. Acad. Sci.* 1990, vol. 87, 1620-1624.
Bell-Parikh et al., "Biosynthesis of 15-deoxy-$\Delta^{12,14}$-PGJ$_2$ and the ligation of PPARγ," *J. Clin. Invest.* 2003, vol. 112, No. 6, 945-955.
Bennett et al., *Cecil Textbook of Medicine* 1996, 20$^{th}$ Ed., vol. 1, 1004-1010.
Bervejillo et al., "Estudio del Potencial Anti-Aterogenico del AANO$_2$ in Vivo," *Tesina del grado de la Licenciatura en Bioquiica, Facultad de Ciencias*, UdelR Feb. 2012, 5-6, Fig. 2 (in Spanish with English summary).
Biegert et al., "Sequence Context-specific Profiles for Homology Searching," *PNAS* 2009, vol. 106, No. 10, 3770-3775.
Bjorn, "Clues emerge about benefits of briefly blocking blood flow," *Nature* Feb. 2009, vol. 15, No. 2, 132.
Blair et al., "Bathophenanthrolinedisulphonic Acid and Bathocuproinedisulphonic Acid, Water Soluble Reagents for Iron and Copper," *Talanta* 1961, vol. 7, Nos. 3-4, 163-174 (abstract).
Blakemore, "The modified Julia olefination: alkene synthesis via the condensation of metallated heteroarylalkylsulfones with carbonyl compounds," *J. Chem. Soc.* Perkin Trans. I, Nov. 4, 2002, 2563-2585.
Blanco et al., "6-Methylnitroarachidonate: A novel esterified nitroalkene that potently inhibits platelet aggregation and exerts cGMP-mediated vascular relaxation," *Free Radic. Biol. Med.* 2011, vol. 50, 411-418.
Bligh et al., "A Rapid Method of Total Lipid Extraction and Purification," *Can. J. Biochem. Physiol.* 1959, vol. 37, No. 8, 911-917.
Bloodsworth et al., "Nitric Oxide Regulation of Free Radical- and Enzyme-Medicated Lipid and Lipoprotein Oxidation," *Arterioscler. Thromb. Vasc. Biol.* Jul. 2000, vol. 20, 1707-1715.
Boden et al., "Free fatty acids in obesity and type 2 diabetes: defining their role in the development of insulin resistance and β-cell dysfunction," *Euro. J. Clin. Invest.* 2002, 32 (Suppl. 3), 14-23.
Bonacci et al., "Gas-Phase Fragmentation Analysis of Nitro-Fatty Acids," *J. Am. Soc. Mass Spec.* 2011, vol. 22, 1534-1551.
Bonacci et al., "Nitro-oleic Acid Improves Insulin Signaling via Protein Tyrosine Phosphatase-1b Inhibition," *Free Radical Bio. Med.* Jan. 1, 2008, Elsevier Science, vol. 45, Suppl. 1, S154 (abstract).
Bonacci et al., "Electrophilic Fatty Acids Regulate Matrix Metalloproteinase Activity and Expression," *J. Biolo. Chem.* 2011, vol. 286, No. 18, 16074-16081 (abstract).
Bonomi et al., "Direct Metal Ion Substitution at the [M(Scys)$_4$]$^2$ Site of Rubredoxin," *J. Biol. Inorg. Chem.* 1998, vol. 3, No. 6, 595-605.
Borniquel et al., "Nitrated oleic acid up-regulates PPARγ and attenuates experimental inflammatory bowel disease," *Free Radic. Bio. Med.* 2010, vol. 49, Iss. 4, 499-505.
Boruwa et al., "Catalytic Asymmetric Henry Reaction," *Tetrahedron: Asymmetry* Dec. 27, 2006, Report No. 90, 17, 3315-3326.
Burdge, "α-Linolenic Acid Metabolism in Men and Women: Nutritional and Biological Implications," *Clin. Nutri. Metabol. Care* 2004, vol. 7, 137-144.

Cannon, *Burger's Medicinal Chemistry and Drug Discovery* 1995, Fifth Edition, vol. I: Principles and Practice, Chap. 19, John Wiley & Sons, Inc., 783-802.
Castro et al., "Cytochrome c: a catalyst and target of nitrate-hydrogen peroxide-dependent protein nitration," *Arch. Biochem. Biophys.* 2004, vol. 421, 99-107.
Chawla et al., "PPAR-γ dependent and independent effects on macrophage-gene expression in lipid metabolism and inflammation," *Nat. Med.* 2001, vol. 7, No. 1, 48-52.
Chen et al., "Peroxisome Proliferator-Activated Receptors and the Cardiovascular System," *Vitam. Horm.* 2003, vol. 66, 157-188.
Chen et al., "Synthesis and Screening of Novel Vitamin E Derivatives for Anticancer Functions," *European J. of Medicinal Chem.* 2012, vol. 58, 72-83.
Chen et al., "Troglitazone Inhibits Aterhosclerosis in Apolipoprotein E-Knockout Mice: Pleiotropic Effects on CD36 Expression and HDL," *Arterioscler. Thromb. Vasc. Biol.* 2001, vol. 21, 372-377.
Clapp et al., "Oxygenation of Monounsaturated Fatty Acids by Soybean Liposygenase-1: Evidence for Transient Hydroperoxide Formation," *Biochem.* 2006, vol. 45, 15884-15892.
Claudel et al., "Reduction of atherosclerosis in apolipoprotein E knockout mice by activation of the retinoid X receptor," *Proc. Natl. Acad. Sci.* 2001, vol. 98, No. 5, 2610-2615.
Coffey et al., "Catalytic consumption of nitric oxide by 12/15-lipoxygenase: Inhibition of monocyte soluble guanylate cyclase activation," *Proc. Natl. Acad. Sci.* Jul. 3, 2001, vol. 98, No. 14, 8006-8011.
Cole et al., "Deciphering the Biology of *Mycobacterium tuberculosis* from the Complete Genome Sequence," *Nature* 1998, vol. 393, 537-544.
Cole et al., "Nitro-Fatty Acid Inhibition of Neointima Formation After Endoluminal Vessel Injury," *Circ. Res.* Nov. 6, 2009, 1-8; Suppl. Materials 1-6.
Coles et al., "Nitrolinoleate Inhibits Platelet Activation by Attenuating Calcium Mobilization and Inducing Phosphorylation of Vasodilator-stimulated Phosphoprotein through Elevation of cAMP," *J. Biol. Chem.* Feb. 22, 2002, vol. 277, No. 8, 5832-5840.
Coles et al., "Nitrolinoleate Inhibits Superoxide Generation, Degranulation, and Integrin Expression by Human Neutrophils. Novel Antiinflammatory Properties of Nitric Oxide-Derived Reactive Species in Vascular Cells," *Circ. Res.* Sep. 6, 2002, vol. 91, 375-381.
Collins et al., "Troglitazone Inhibits Formation of Early Atherosclerotic Lesions in Diabetic and Nondiabetic Low Density Lipoprotein Receptor-Deficient Mice," *Arterioscler. Thromb. Vasc. Biol.* 2001, vol. 21, 365-371.
Cosby et al., "Nitrite reduction to nitric oxide by deoxyhemoglobin vasodilates the human circulation," *Nat. Med.* 2003, vol. 9, No. 12, 1498-1505.
Cowley et al., "The *Mycobacterium tuberculosis* Protein Serine/threonine Kinase PknG is Linked to Cellular Glutamate/glutamine Levels and is Important for Growth In Vivo," *Molecular Microbio.* 2004, vol. 52, No. 6, 1691-1702.
Cui et al., "Nitrated Fatty Acids: Endogenous Anti-inflammatory Signaling Mediators," *J. Biol. Chem.* Nov. 24, 2006, vol. 281, No. 47, 35686-35698.
Dang et al. (Hung), "Anti-inflammatory Constituents of the Red Alga *Gracilaria verrucosa* and Their Synthetic Analogues," *J. Nat. Prod.* 2008, vol. 71, No. 2, 232-240.
Dangi et al., "Biogenic Synthesis, Purification, and Chemical Characterization of Anti-Inflammatory Resolvins Derived from Docosapentaenoic Acid (DPAn-6)," *J. Biol. Chem.* May 29, 2009, vol. 284, No. 22, 14744-14759.
Davies et al., "Oxidized Alkyl Phospholipids Are Specific, High Affinity Peroxisome Proliferator-activated Receptor γ Ligands and Agonists," *J. Biol. Chem.* May 11, 2001, vol. 276, No. 19, 16015-16023.
Defronzo et al., "Insulin Resistance: A Multifaceted Syndrome Responsible for NIDDM, Obesity, Hypertension, Dyslipidemia, and Atherosclerotic Cardiovascular Disease," *Diabetes Care* Mar. 1991, vol. 14, No. 3, 175-194.

(56) References Cited

OTHER PUBLICATIONS

Delerive et al., "Oxidized Phospholipids Activated PPARα in a Phospholipase A2-Dependent Manner," *FEBS Lett.* 2000, vol. 471, 34-38.
Del Mar Grassa et al., "Daily Oral Oleoyl-estrone Gavage Induces a Dose-dependent Loss of Fat in Wistar Rats," *Obesity Res.* Mar. 1, 2001, vol. 9, No. 3, 202-209.
Dembitsky et al., "Natural halogenated fatty acids: their analogues and derivatives," *Progress in Lipid Research* 2002, vol. 41, No. 4, 315-367.
De Meijere et al., "Metal-Catalyzed Cross-Coupling Reactions," *Wiley-VCH Verlag GMbH & Co.* 2004, Weinheim, Vols. 1 and 2, XXII, ISBN-10: 3-527-30518-1 and ISBN-13: 978-3-527-30518-6 (TOC).
Denicola et al., "Diffusion of Nitric Oxide into Low Density Lipoprotein," *J. Biol. Chem.* 2002, vol. 277, No. 2, 932-936.
Denicola et al., "Diffusion of peroxynitrite across erythrocyte membranes," *Proc. Natl. Acad. Sci.* 1998, vol. 95, 3566-3571.
Desper et al., "Getting a Tree Fast: Neighbor Joining, FastME, and Distance-Based Methods," *Curr. Protoc. Bioinformatics* 2006, Chap. 6, Unit 6.3.
Diabetic ketoacidosis in www.mayoclinic.org/diseases-conditions/diabetic-ketoacidosis/basics/treatment/con-20026470 (retrieved from the internet Jan. 21, 2016).
d'Ischia, "Oxygen-Dependent Nitration of Ethyl Linoleate with Nitric Oxide," *Tetrahedron Lett.* 1996, vol. 37, No. 32, 5773-5774.
d'Ischia et al., "Medium-dependent Competitive Pathways in the Reactions of Polyunsaturated Fatty Acids with Nitric Oxide in the Presence of Oxygen. Structural Characterisation of Nitration Products and a Theoretical Insight," *Tetrahedron* 1999, vol. 55, 9297-9308.
Dodge et al., "Composition of phospholipids and of phospholipids fatty acids and aldehydes in human red cells," *J. Lipid Res.* 1967, vol. 8, 667-675.
Doksorubitsin-Ebeve, Instruksiya po primeneniyu lekarstvennogo perparata dlya meditinskogo primeneniya, Retrieved from the Internet: Nov. 19, 2014, http://medi.ru/doc/f4509.htm.
Dorwald, "Side reactions in Organic Synthesis," 2005, Wiley-VCH, 1-16.
Duan et al., "Nephrotoxicity of high- and low-osmolar contrast media: Protective role of forsinopril or telmisartan in a rat model," *J. Central S. Univ.* (Dec. 31, 2007), vol. 32, No. 5, 812-818.
Easton et al., "Polyunsaturated Nitroalkanes and Nitro-Substituted Fatty Acides," *Synthesis* 2001, vol. 3, 451-457.
Eberhardt et al., "Prevalence of Overweight and Obesity Among Adults with Diagnosed Diabetes—United States, 1988-1994 and 1999-2002," *CDC*, Nov. 19, 2004; vol. 53, No. 45, 1066-1068.
Eiserich et al., "Myeloperoxidase, a Leukocyte-Derived Vascular NO Oxidase," *Sci.* Jun. 28, 2002, vol. 296, 2391-2394.
Eiserich et al., "Pathophysiology of Nitric Oxide and Related Species: Free Radical Reactions and Modification of Biomolecules," *Molec. Aspects Med.* 1998, vol. 19, 221-357.
EP Communication issued on European Patent Application No. 09767748.8 dated Dec. 27, 2011.
Escudier et al., "Bevacizumab plus interferon alfa-2a for treatment of metastatic renal cell carcinoma: a randomized, double-blind phase III trial," *The Lancet* Dec. 22/29, 2007, vol. 370, 2103-2111.
European Examination Report issued in corresponding foreign application, EP Appl. 09767748.8, 1-3, dated Oct. 23, 2012.
Evans et al., "PPARs and the complex journey to obesity," *Nat. Med.* Apr. 2004, vol. 10, No. 4, 1-7.
Extended European Search Report and Written Opinion issued in corresponding foreign application, EP 10821313.3, 1-9 (Jul. 2013).
Extended European Search Report and Written Opinion issued in corresponding foreign application, EP 11804082.3, 1-5 (Nov. 29, 2013).
Extended European Search Report and Written Opinion issued in corresponding European Patent Application No. 12825790.4, 1-7 (Dec. 11, 2014).
Extended European Search Report and Written Opinion issued in corresponding European Patent Application No. 12839555.5, 1-6 (Feb. 2, 2015).
Extended European Search Report and Written Opinion issued in European Patent Application No. 09767748.8, 1-6, dated Dec. 8, 2011.
Extended European Search Report and Written Opinion issued in EP Patent Application No. 09732031.1 dated Dec. 22, 2011.
Extended European Search Report and Written Opinion issued in EP Patent Application No. 13743207.6-1464, dated Jun. 22, 2015.
Extended European Search Report and Written Opinion issued in corresponding European Patent Application No. 16157509.7, 1-9 (May 30, 2016).
Feelisch et al., "Concomitant S-, N-, and heme-nitros(yl)ation in biological tissues and fluids: implications for the fate of NO in vivo," *FASEB J.* Nov. 2002, vol. 16, 1775-1785.
Ferreira et al., "Macrophage activation induces formation of the anti-inflammatory lipid cholesteryl-nitrolinoleate," *Biochem. J.* 2009, vol. 417, 223-234.
Ferry et al., "Binding of prostaglandins to human PPARγ: tool assessment and new natural ligands," *Eur. J. Pharmacol.* 2001, vol. 417, 77-89.
Finlayson-Pitts et al., "A Fourier Transform Infrared Spectrometry Study of the Reactions of Phosphatidylcholines with Gaseous $N_2O_5$ and $NO_2$," *Toxicol. Appl. Pharmacol.* 1987, vol. 89, 438-448.
Fiuza et al., "From the Characterization of the Four Serine/Threonine Protein Kinases (PknA/B/G/L) of Corynebacterium Glutamicum Toward the Role of PknA and PknB in Cell Division," *J. Biolo. Chem.* 2008, vol. 283, No. 26, 10899-18112.
Forman et al., "15-Deoxy-$\Delta^{12-14}$-Prostaglandin $J_2$ is a Ligand for the Adipocyte Determination Factory PPARγ," *Cell* 1995, vol. 83, 803-812.
Freeman et al., "Nitro-fatty Acid Formation and Signaling," *J. of Biol. Chem.* Jun. 6, 2008, vol. 283, No. 23, 15515-15519.
Freshney, "Culture of Animal Cells," *A Manual of Basic Technique* 1983, Alan R. Liss, Inc., New York, 1-6.
Fu et al., "Oleylethanolamide regulates feeding and body weight through activation of the nuclear receptor PPAR-α," *Nature* Sep. 4, 2003, vol. 425, 90-93.
Furstner et al., "Total Synthesis of Epohelmin B and Its Analogues," *Chem. Asian J.* 2008, vol. 3, 310-318.
Gallon et al., "The Identification of the Allylic Nitrite and Nitro Derivatives of Methyl Linoleate and Methyl Linolenate by Negative Chemical Ionization Mass Spectroscopy," *Lipids* 1993, vol. 28, No. 2, 125-133.
Gallon et al., "The Reaction of Low Levels of Nitrogen Dioxide with Methyl Linoleate in the Presence and Absence of Oxygen," *Lipids* 1994, vol. 29, No. 3, 171-176.
Gavin III et al., "Reducing Cardiovascular Disease Risk in Patients with Type 2 Diabetes: A Message from the National Diabetes Education Program," *Am. Fam. Physician* Oct. 15, 2003, vol. 68, No. 8, 1569-74.
Gladwin et al., "The emerging biology of the nitrite anion," *Nature* Nov. 2005, vol. 1, No. 6, 308-314.
Gladwin et al., "Role of circulating nitrite and S-nitrosohemoglobin in the regulation of regional blood flow in humans," *Proc. Natl. Acad. Sci.* 2000, vol. 97, No. 21, 11482-11487.
Gladwin et al., "S-Nitrosohemoglobin Is Unstable in the Reductive Erythrocyte Environment and Lacks $O_2$/NO-linked Allosteric Function," *J. Biol. Chem.* 2002, vol. 277, No. 31, 27818-27828.
Glauser et al., "The inflammatory response and tissue damage. The example of renal scars following acute renal infection," *Pediatric Nephrology* Oct. 1987, vol. 1, No. 4, 615-622 (Abstract) (from PubMed website Jan. 22, 2016).
Goodman & Gilman's *The Pharmacological Basis of Therapeutics*, Sixth Edition 1980, MacMillan Publishing Co., New York (TOC).
Goodman & Gilman's *The Pharmacological Basis of Therapeutics*, Ninth Edition 1996, McGraw-Hill Book Company, New York, Appendix II, 1707-1711 (TOC).
Goodman & Gilman's *The Pharmacological Basis of Therapeutics*, Tenth Edition 2001, McGraw-Hill Book Company, New York (TOC).

(56) References Cited

OTHER PUBLICATIONS

Gorczynski et al., "Evaluation of Nitroalkenes as Nitric Oxide Donors," *Bioorg. Med. Chem. Lett.* 2007, vol. 17, 2013-2017.
Gorczynski et al., "Regio-and Stereospecific Synthesis and Nitric Oxide Donor Properties of ε-9- and ε-10-Nitrooctadec-9-enoic Acids," *Org. Lett.* Apr. 25, 2006, vol. 8, No. 11, 2305-2308.
Gregory et al., "5-$HT_3$ Receptor Antogonists for the Prevention of Chemotherapy-Induced Nausea and Vomiting: A Comparison of Their Pharmacoogy and Clinical Efficacy," *Drugs* Feb. 1998, vol. 55, No. 2, 173-189.
Grisham, "Myoglobin-Catalyzed Hydrogen Peroxide Dependent Arachidonic Acid Peroxidation," *Free Radic. Biol. Med.* 1985, vol. 1, 227-232.
Groeger et al., "Discovery, Structural Characterization and Quantification of Novel Inflammatory-Induced Electrophilic Fatty Acid Derivatives," *Free Radical Bio. & Med.* 2008, vol. 45, No. 1, S134.
Groeger et al., "Cyclooxygenase-2 generates anti-inflammatory mediators from omega-3 fatty acids," *Nat. Chem. Bio.* Jun. 2010, vol. 6, 433-441.
Groeger et al., "Signaling Actions of Electrophiles: Anti-inflammatory Therapeutic Candidates," *Molec. Interven.* Feb. 2010, vol. 10, Issue 1, 39-50.
Guindon et al., "A Simple, Fast, and Accurate Algorithm to Estimate Large Phylogenies by Maximum Likelihood," *Systematic Bio.* 2003, vol. 52, No. 5, 696-704.
Guindon et al., "Estimating Maximum Likelihood Phylogenies with PhyML," *Methods in Molecular Bio.* 2009, vol. 537, 113-137.
Guo et al., "Atypical PKCζ transduces electrophilic fatty acid signaling in pulmonary epithelial cells," *Nitric Oxide* 2011, vol. 25, 366-372.
Gutierrez et al., "Nitric Oxide Regulation of Superoxide-Dependent Lung Injury: Oxidant-Protective Actions of Endogenously Produced and Exogenously Administered Nitric Oxide," *Free Radic. Biol. Med.* 1996, vol. 21, No. 1, 43-52.
Hartmann et al., "A randomized trial comparing the nephrotoxicity of cisplatin/ifosfamide-based combination chemotherapy with or without amifostine in patients with solid tumors," *Investigational New Drugs* 2000, vol. 18, 281-289.
Hogg et al., "Reactions of Nitric Oxide With Nitronyl Nitroxides and Oxygen: Prediction of Nitrate Formation by Kinetic Simulation," *Free Radic. Res.* 1995, vol. 22, No. 1, 47-56.
Hogg et al., "Inhibition of low-density lipoprotein oxidation by nitric oxide Potential role in atherogenesis," *FEBS Lett.* 1993, vol. 334, No. 2, 170-174.
Hogg, "The Biochemistry and Physiology of S-nitrosothiols," *Annu. Rev. Pharmacol. Toxicol.* 2002, 42, 585-600.
Ichikawa et al., "Nitroalkenes Suppress Lipopolysaccharide-Induced Signal Transducer and Activator of Transcription Signaling in Macrophages: A Critical Role of Mitogen-Activated Protein Kinase Phosphatase 1," *Endocrinology* May 8, 2008, vol. 149, No. 8, 4086-4094.
Ignarro et al., "Endothelium-Derived Relaxing Factor From Pulmonary Artery and Vein Possesses Pharmacologic and Chemical Properties Identical to Those of Nitric Oxide Radical," *Circ. Res.* 1987, vol. 61, 866-879.
Ignarro et al., "Pharmacological Evidence that Endothelium-Derived Relaxing Factor is Nitric Oxide: Use of Pyrogallol and Superoxide Dismutase to Study Endothelium-Dependent and Nitric Oxide-Elicted Vascular Smooth Muscle Relaxation," *J. Pharmacol. ExTher.* 1988, vol. 244, No. 1, 181-189.
Iles et al., "Fatty acid transduction of nitric oxide signaling: nitrolinoleic acid mediates protective effects through regulation of the ERK pathway," *Free Radic. Biol. Med.* 2009, vol. 46, 866-875.
International Preliminary Report on Patentability for PCT/US2009/0047825 dated Jan. 6, 2011.
International Preliminary Report on Patentability issued in corresponding PCT/US2012/051304, 1-8 (Mar. 6, 2014).
International Preliminary Report on Patentability issued in corresponding PCT/US2012/059722, 1-9 (Apr. 24, 2014).
International Search Report and Written Opinion dated Dec. 4, 2009, in corresponding PCT/US2009/002628.
International Search Report and Written Opinion mailed Apr. 21, 2015 corresponding to PCT/US2014/065203.
International Search Report and Written Opinion mailed Aug. 19, 2013 corresponding to PCT/US2012/059722.
International Search Report and Written Opinion mailed Jul. 13, 2011 corresponding to PCT/US2010/051059.
International Search Report and Written Opinion mailed Jun. 2, 2013 corresponding to PCT/US2013/024476.
International Search Report and Written Opinion mailed Jun. 30, 2009 corresponding to PCT/US2009/041018.
International Search Report and Written Opinion mailed Mar. 23, 2012 corresponding to PCT/US2011/042011.
International Search Report and Written Opinion mailed Mar. 5, 2010 corresponding to PCT/US2009/047825.
International Search Report and Written Opinion mailed Nov. 1, 2012 corresponding to PCT/US2012/051304.
International Search Report and Written Opinion mailed Nov. 27, 2014 corresponding to PCT/US2014/047073.
International Search Report and Written Opinion mailed Oct. 12, 2006 corresponding to International Patent Application No. PCT/US2005/014305.
International Search Report PCT/US2010/002141 dated Nov. 24, 2010.
Itoh et al., "Synthesis of Docosahexaenoic Acid Derivatives Designed as Novel PPARγ Agonists and Antidiabetic Agents," *Bioorg. Med. Chem.* 2006, vol. 14, 98-108.
Janero et al., "Differential nitros(yl)ation of blood and tissue constituents during glyceral trinitrate biotransformation in vivo," PNAS Nov. 30, 2004, vol. 101, No. 48, 16958-16963.
Jeong et al., "Fenofibrate Prevents Obesity and Hypertriglyceridemia in Low-Density Lipoprotein Receptor-Null Mice," *Metabolism* May 2004, vol. 53, No. 5, 607-613.
Jimenez-Estrada et al., "Allyic Nitration of 3β-Sitosterol and Cholesterol Acetate: Preparation of 7-Nitro Derivatives," *Steroid* Jun. 1997, vol. 62, 500-503.
Jourd'Heuil et al., "The Oxidative and Nitrosative Chemistry of the Nitric Oxide/Superoxide Reaction in the Presence of Bicarbonate," *Arch. Biochem. Biophys.* 1999, vol. 365, No. 1, 92-100.
Junping et al., "Pharmacokinetics and antitumor effects of vincristine carried microemulsions composed of PEG-lipid, oleic acid, vitamin E and cholesterol," *Int. J. Pharm.* Jan. 30, 2003, vol. 251, No. 1-2, 13-21, abstract provided.
Kansanen et al., "Nrf2-Dependent and -Independent Responses to Nitro-fatty Acids in Human Endothelial Cells: Identification of Heat Shock Response as the Major Pathway Activated by Nitro-oleic Acid," *J. Biol. Chem.* Oct. 5, 2009, 1-34.
Karp et al., "Clinical and Biologic Activity of the Farnesyltransferase Inhibitor R115777 in Adults with Refractory and Relapsed Acute Leukemias: A Phase 1 Clinical-Laboratory Correlative Trial," *Blood* Jun. 2001, vol. 97, No. 11, 3361-3369.
Katoh et al., "Recent Developments in the MAFFT Multiple Sequence Alignment Program," *Briefings in Bioinformatics* 2008, vol. 9, No. 4, 286-298.
Kelley et al., "Nitro-oleic Acid, a Novel and Irreversible Inhibitor of Xanthine Oxidoreductase," *J. Biol. Chem.* Dec. 28, 2008, vol. 283, No. 52, 36176-36184.
Khoo et al., "Activation of vascular endothelial nitric oxide synthase and heme oxygenase-1 expression by electrophilic nitro-fatty acids," *Free Radic. Bio. Med.* 2010, vol. 48, 230-239.
Khoo et al., "Electrophilic nitro-fatty acids: anti-inflammatory mediators in the vascular compartment," *Curr. Opn. Pharml.* 2010, vol. 10, 179-184.
Kim et al., "Bisubstrate Ketone Analogues as Serotonin N-Acetyltransferase Inhibitors," *J. Med. Chem.* 2001, vol. 44, No. 15, 2479-2485.
Kissner et al., "Formation and Properties of Peroxynitrite as Studied by Laser Flash Photolysis, High-Pressure Stopped-Flow Technique, and Pulse Radiolysis," *Chem. Res. Toxicol.* Sep. 4, 1997, vol. 10, 1285-1292.

(56) References Cited

OTHER PUBLICATIONS

Kliewer et al. "A Prostaglandin $J_2$ Metabolite Binds Peroxisome Proliferatory-Activated Receptor γ and Promotes Adipocyte Differentiation," *Cell* 1995, vol. 83, 813-819.
Kliewer et al., "Fatty acids and eicosanoids regulate gene expression through direct interactions and peroxisome proliferator-activated receptors α and γ," *Proc. Natl. Acad. Sci.* Apr. 1997, vol. 94, 4318-4323.
Kobayshi, "The Reaction of Nitrogen Dioxide with Lung Surface Components: The Reaction with cis-9-octadecenoic Acid," *Chemosphere* 1983, vol. 12, No. 9/10, 1317-1325.
Koenitzer et al., "Redox signaling in inflammation: interactions of endogenous electrophiles and mitochondria in cardiovascular disease," *Ann. N.Y. Acad. Sci.* 2010, vol. 1203, 45-52.
Kunin, "Urinary Tract Infections in Females," *Clinical Infectious Diseases*, Jan. 1994, vol. 18, 1-10.
Lai et al., "Reactions of Dinitrogen Pentoxide and Nitrogen Dioxide with 1-Palmitoyl-2-Oleoyl-sn-Glycero-3-Phosphocholine," *Lipids* 1991, vol. 26(4), 306-314. Abstract.
Lärfars et al., "Activation of Nitric Oxide Release and Oxidative Metabolism by Leukotrienes B4, C4, and D4 in Human Polymorphonuclear Leukocytes," *Blood* Feb. 15, 1999, vol. 93, No. 4, 1399-1405.
Lee et al., "Rosiglitazone ameliorates cisplatin-induced renal injury in mice," *Nephrol. Dial. Transplant.* 2006, vol. 21, 2096-2105.
Lee et al., "Peroxisome proliferators-activated receptor-γ in macrophage lipid homeostasis," *Trends Endocrinol. Metab.* Oct. 2002, vol. 13, No. 8, 331-335.
Levy et al., "Lipid mediator class switching during acute inflammation: signals in resolution," *Nat. Immunol.* Jul. 2001, vol. 2, No. 7, 612-619.
Li et al., "Molecular recognition of nitrated fatty acids by PPARγ," *Nat. Struct. Mol. Biol.* 2008, 1-3.
Li et al., "Differential inhibition of macrophage foam-cell formation and atherosclerosis in mice by PPARalpha, betta/delta, and gamma," *J. Clin. Invest.* 2004, vol. 114, No. 11, 1564-1576.
Li et al., "PPARα Ligand Protects During Cisplatin-Induced Acute Renal Failure by Preventing Inhibition of Renal FAO and PDC Activity," *Am. J. Physiol. Renal Physiol.* Mar. 2004, vol. 286, F572-F580.
Lim et al., "Nitrolinoleate, a nitric oxide-derived mediator of cell function: Synthesis, characterization, and vasomotor activity," *Proc. Natl. Acad. Sci.* Dec. 10, 2002, vol. 99, No. 25, 15941-15946.
Lima et al., "Characterization of Linoleic Acid Nitration in Human Blood Plasma by Mass Spectrometry," *Biochem.* 2002, vol. 41, No. 34, 10717-10722.
Lima et al., "Cholesteryl Nitrolinoleate, a Nitrated Lipid Present in Human Blood Plasma and Lipoproteins," *J. Lipid Res.* 2003, vol. 44, 1660-1666.
Lima et al., "Nitrated Lipids Decompose to Nitric Oxide and Lipid Radicals and Cause Vasorelaxation," *Free Radical Bio. Med.* 2005, Elsevier Sciences, vol. 39, No. 4, 532-539.
Liu et al., "Accelerated reaction of nitric oxide with $O_2$ within the hydrophobic interior of biological membranes," *Proc. Natl. Acad. Sci.* Mar. 1998, vol. 95, 2175-2179.
Liu et al., "Combined losartan and nitro-oleic acid remarkably improves diabetic nephrophaty in mice," *Am. J. Physiol. Renal Physiol.* Aug. 14, 2013, vol. 305, F1555-F1562.
Liu et al., "Nitrol-Oleic Acid Protects the Mouse Kidney from Ischemia and Reperfusion Injury," *Am. J. Physiol. Renal Physiol.* Oct. 2008, vol. 295, No. 4, F942-F949.
Lopez et al., "Second Generation of α-Tocopherol Analogs—Nitric Oxide Donors: Synthesis, Physiochemical, and Biological Characterization," *Bioorg. Med. Chem.* 2007, vol. 15, 6262-6272.
Löytynoja et al., "An Algorithm for Progressive Multiple Alignment of Sequences with Insertions," *PNAS* Jul. 26, 2005, vol. 102, No. 30, 10557-10562.
Lundberg et al., "Nitrate and nitrite in biology, nutrition and therapeutics," *Nat. Chem. Bio.* Dec. 2009, vol. 5, No. 12, 865-869.
Luzzio, "The Henry reaction: recent examples," *Tetrahedron* 2001, vol. 57, 915-945.
Ma et al., "Hydrohalogenation Reaction of Substituted 1, 2-Allenic Carboxylic Acids, Esters, Amides, Nitriles, and Diphenyl Phosphine Oxides," *Synthesis* Dec. 4, 2001, No. 5, 713-730.
Manini et al., "Chemistry of Nitrated lipids: Remarkable Instability of 9-Nitrolinoleic Acid in Neutral Aqueous Medium and a Novel Nitronitrate Ester Product by Concurrent Autoxidation/Nitric Oxide-Release Pathways," *J. Org. Chem.* (2008), vol. 73, No. 19, 7517-7525.
March, "Effects of Structure on Reactivity," *Advanced Organic Chemistry* (1977 edition), McGraw-Hill Book Company, New York, 251-259.
Marnett et al., "Regulation of Prostaglandin Biosynthesis by Nitric Oxide Is Revealed by Targeted Deletion of Inducible Nitric-oxide Synthese," *J. Biol. Chem.* 2000, vol. 275, No. 18, 13427-13430.
Marshall et al., "Nitrosation and oxidation in the regulation of gene expression," *FASEB J.* 2000, vol. 14, 1889-1900.
McIntyre et al., "Identification of an intracellular receptor for lysophosphatidic acid (LPA): LPA is a transcellular PPARγ agonist," *Proc. Natl. Acad. Sci.* 2003, vol. 100(1), 131-136.
McLean, "Iodostarin," *Archives of Internal Medicine* 1912, vol. 10, 509.
Menendez et al., "Effects of gama-linolenic acid and oleic acid on paclitaxel cytotoxicity in human breast cancer cells," *European J. of Cancer* (Oxford, England: 1990) Feb. 2001, vol. 37, No. 3, 402-213.
Messerschmidt et al., *Handbook of Metalloproteins* 2001, Hoboken, NJ, John Wiley & Sons, Inc. (abstract).
Metabolite definition at https://www.nlm.nih.gov/medlineplus/ency/article/002258.htm (retrieved from the internet Jan. 21, 2016).
Meyer et al., "Uremia," *New Engl. J. Med.* Sep. 27, 2007, vol. 357, 1316-1325.
Minghetti, "Cyclooxygenase-2 (COX-2) in Inflammatory and Degenerative Brain Diseases," *J. Neuropathol. Exp. Neurol.* Sep. 2004, vol. 63, No. 9, 901-910.
Miranda et al., "The Chemical Biology of Nitric Oxide," *Nitric Oxide: Biology and Pathobiology* 2000, Academic Press, San Diego, 41-55.
Montuschi et al., "Isoprostanes: markers and mediators of oxidative stress," *FASEB J.* Dec. 2004, vol. 18, 1791-1800.
Morgan et al., "Use of Animal Models of Human Disease for Nonclinical Safety Assessment of Novel Pharmaceuticals," *Toxicol. Pathol.* 2013, vol. 41, No. 3, 508-518.
Mukherjee et al., "A Selective Peroxisome Proliferator-Activated Receptor-γ (PPARγ) Modulatory Blocks Adipocyte Differentiation byt Stimulates Glucose uptake in 3T3-L1 Adipocytes," *Mol. Endocrinol.* 2000, vol. 14, 1425-1433.
Nadtochiy et al. "Mitochondrial nitroalkene formation and mild uncoupling in ischaemic preconditioning: implications for cardioprotection," *Card. Res. Adv. Access* 2008, 1-8.
Nadtochiy et al., "Nitroalkenes Confer Acute Cardioprotection via Adenine Nucleotide Transloase 1," *J. Biol. Chem.* Jan. 27, 2012, vol. 287, No. 5, 3573-3580.
Nagano et al., "Use of tacrolimus, a potent antifibrotic agent, in bleomycin-induced lung fibrosis," *Eur. Respir. J.* 2006, vol. 27, 460-469.
Nagy et al., "Oxidized LDL Regulates Macrophage Gene Expression through Ligand Activation of PPARγ," *Cell* 1998, vol. 93, 229-240.
Napolitano et al., "Acid-Promoted Reactions of Ethyl Linoleate with Nitrite Ions: Formation and Structural Characterization of Isomeric Nitroalkene, Nitrohydroxy, and Novel 3-Nitro-1,5-hexadiene and 1,5-Dinitro-1,3-pentadiene Products," *J. Org. Chem.* 2000, vol. 65, No. 16, 4853-4860.
Napolitano et al., "The acid-promoted reaction of ethyl linoleate with nitrite. New insights from $^{15}$N-labelling and peculiar reactivity of a model skipped diene," *Tetrahedron* 2002, vol. 58, 5061-5067.
Napolitano et al., "Acid-Induced Structural Modifications of Unsaturated Fatty Acids and Phenolic Olive Oil Constituents by Nitrite Ions: A Chemical Assessment," *Chem. Res. Toxicol.* 2004, vol. 17, 1329-1337.

(56) References Cited

OTHER PUBLICATIONS

Narayan et al., "Serine Threonine Protein Kinases of Mycobacterial Genus: Phylogeny to Function," *Physiological Genomics* 2007, vol. 29, 66-75.

Nathan, "Nitric oxide as a secretory product of mammalian cells," *FASEB J.* 1992, vol. 6, 3051-3064.

Newman et al., "Optimized Thiol Derivatizing Reagent for the Mass Spectral Analysis of Distributed Epoxy Fatty Acids," *J. Chromato.* May 22, 2011, No. 925, 223-240.

Niebisch et al., "Corynebacterial Protein Kinase G Controls 2-Oxoglutarate Dehydrogenase Activity via the Phosphorylation Status of the Odhl Protein," *J. Biolo. Chem.* 2006, vol. 281, No. 18, 12300-12307.

Notredame et al., "T-Coffee: A novel method for fast and accurate multiple sequence alignment," *J. Molec. Bio.* 2000, vol. 302, 205-217.

Nott et al., "An Intramolecular Switch Regulates Phosphoindependent FHA Domain Interactions in *Mycobacterium tuberculosis*," *Sci. Signaling* 2009, vol. 2, No. 63, ra 12.

O'Donnell et al., "Interactions Between Nitric Oxide and Lipid Oxidation Pathways: Implications for Vascular Disease," *Circ. Res.* 2001, vol. 88, 12-21.

O'Donnell et al., "15-Lipoxygenase Catalytically Consumes Nitric Oxide and Impairs Activation of Guanylae Cyclase," *J. Biol. Chem.* Jul. 16, 1999, vol. 274, No. 29, 20083-20091.

O'Donnell et al., "Catalytic Consumption of Nitric Oxide by Prostagladin H Synthase-1 Regulates Platelet Function," *J. Biol. Chem.* Dec. 8, 2000, vol. 275, No. 49, 38239-38244.

O'Donnell et al., "Nitration of Unsaturated Fatty Acids by Nitric Oxide-Derived Reactive Nitrogen Species Peroxynitrite, Nitrous Acid, Nitrogen Dioxide, and Nitronium Ion," *Chem. Res. Toxicol.* 1999, vol. 12, No. 1, 83-92.

O'Donnell et al., "Nitric Oxide Inhibition of Lipid Peroxidation: Kinetics of Reaction with Lipid Peroxyl Radicals and Comparison with α-Tocopherol," *Biochem.* 1997, vol. 36, No. 49, 15216-15223.

O'Hare et al., "Regulation of Glutamate Metabolism by Protein Kinases in Mycobacteria," *Mol. Microbio.* 2008, vol. 70, No. 6, 1408-1423.

Ono et al., "A Convenient Procedure for the Conversion ε-Nitroalkenes to (Z)-Nitroalkenes via erythro-β-Nitroselenides," *J. Chem. Soc., Chem Commun.* 1987, 1550-1551.

Ortiz-Lombardia et al., "Crystal Structure of the Catalytic Domain of the PknB Serine/Threonine Kinase from Mycobacterium Tuberculosis," *J. Biolo. Chem.* 2003, vol. 278, No. 15, 13094-13100.

Padmaja, "The Reaction of Nitric Oxide With Organic Peroxyl Radicals," *Biochem. Biophys. Res. Commun.* 1993, vol. 195, No. 2, 539-544.

Park et al., "Modulation of Tumor Necrosis Factor-Related Apoptosis-Inducing Ligand-Induced Apoptosis by Chemotherapy in Thyroid Cancer Cell Lines," *Thyroid* 2003, vol. 13. No. 12, 1103-1110.

Pawliczak et al., "85-kDa Cytosolic Phospholipase $A_2$ Mediates Peroxisome Proliferator-activated Receptor γ Activation in Human Lung Epithelial Cells," *J. Biol. Chem.* 2002, vol. 277, 33153-33163.

*Pharma Medica* (2002), 20(5):1999-210 (in Japanese with brief English relevance).

Pryor et al., "Reaction of Nitrogen Dioxide with Alkenes and Polyunsaturated Fatty Acids: Addition and Hydrogen Abstraction Mechanisms," *J. Amer. Chem. Soc.* 1982, vol. 104, 6685-6692.

Punchard et al., The Journal of Inflammation Editorial, Sep. 27, 2004, *The Journal of Inflammation*, BioMed Central, vol. 1, No. 1, 1-4.

Quijano et al., "Reaction of Peroxynitrite with Mn-Superoxide Dismutase: Role of the Metal Center in Decomposition Kinetics and Nitration," *J. of Biol. Chem.* Apr. 13, 2001, vol. 276, No. 15, 11631-11638.

Radi et al., "Peroxynitrite Oxidation of Sulfhydryls: The Cytotoxic Potential of Superoxide and Nitric Oxide," *J. Biol. Chem.* 1991, vol. 266, No. 7, 4244-4250.

Radi et al., "Peroxynitrite Reactions with Carbon Dioxide-Bicarbonate," *Methods Enzymol.* 1999, vol. 301, No. 37, 353-367.

Ranu et al., "Highly Selective Reduction of Conjugated Nitroalkenes with Zinc Borohydride in DME," *Tetrahedron Letters* 1991, vol. 32, No. 29, 3579-3582.

Rassaf et al., "Concomitant Presence of N-Nitroso and S-Nitroso Proteins in Human Plasma," *Free Radic. Biol. Med.* 2002, vol. 33, No. 11, 1590-1596.

Rassaf et al., "NO adducts in mammalian red blood cells: too much or too little?" *Nat. Med.* 2003, vol. 9, No. 5, 481-482.

Remington's *Pharmaceutical Sciences* 1990, 18th Ed. (TOC).

Rosen et al., "PPARγ: a Nuclear Regulator of Metabolism, Differentiation, and Cell Growth," *J. Biol. Chem.* 2001, vol. 276, No. 1, 37731-37734.

Rowe et al., "Acesulfame Potassium," *Handbook of Pharma. Excipients* 2006, $5^{th}$ Ed., Great Britain: Pharmaceutical Press (abstract).

Rowe et al., *Handbook of Pharma. Excipients* 2006, $5^{th}$ Ed., Great Britain: Pharmaceutical Press, American Pharmacists Association.

Rubbo et al., "Form on Nitric Oxide: Chemical Events in Toxicity. Nitrix Oxide Regulation of Tissue Free Radical Injury," *Chem. Res. Toxicol.* 1996, vol. 9, No. 5, 809-820.

Rubbo et al., "Nitric Oxide Inhibition of Lipoxygenase-Dependent Liposome and Low-Density Lipoprotein Oxidation: Termination of Radical Chain Propagation Reactions and Formation of Nitrogen-Containing Oxidized Lipid Derivatives," *Arch. Biochem. Biophys.* Dec. 1, 1995, vol. 324, No. 1, 15-25.

Rubbo et al., "Nitric Oxide Reaction with Lipid Peroxyl Radicals Spares α-Tocopherol during Lipid Peroxidation," *J. Biol. Chem.* 2000, vol. 275, No. 25, 10812-10818.

Rubbo et al., "Nitric Oxide Regulation of Superoxide and Peroxynitrite-dependent Lipid Peroxidation," *J. Biol. Chem.* Oct. 21, 1994, vol. 269, No. 42, 26066-26075.

Rudnick et al., "Contrast-induced nephropathy: How it develops, how to prevent it," *Cleveland Clinic J. Med.* Jan. 2006, vol. 73, No. 1, 75-87.

Rudolph et al., "Cardiovascular Consequences When Nitric Oxide and Lipid Signaling Converge," *Circ. Res.* Sep. 11, 2009, vol. 105, 511-522.

Rudolph et al., "Endogenous generation and protective effects of nitro-fatty acids in murine model of focal cardiac ischaemia and reperfusion," *Cardiov. Res. Advance Access* 2009, 1-12.

Rudolph et al., "Nitro-fatty Acid Metabolome: Saturation, Desaturation, β-Oxidation, and Protein Adduction," *J. Biol. Chem.* Jan. 16, 2009, vol. 284, No. 3, 1461-1473.

Rudolph et al., "Nitro-Fatty Acids Reduce Atherosclerosis in Apolipoprotein E-Deficient Mice," *Ather. Thromb. Vasc. Bio.* May 2010, vol. 30, 938-945.

Rudolph et al., "Transduction of Redox Signaling by Electrophile-Protein Reactions," *Sc. Signaling* Sep. 29, 2009, vol. 2, Issue 90 re7, 1-13.

Saffer et al., "Choosing Drug Therapy for Patients with Hyperlipidemia," *Am. Fam. Physic.* Jun. 1, 2000, vol. 61, No. 11, 3371-3382.

Sarver et al., "Analysis of Peptides and Proteins Containing Nitrotyrosine by Matrix-assisted Laser Desorption/ionization Mass Spectrometry," *J. Am. Soc. Mass Spectrom.* 2001, vol. 12, No. 4, 439-448.

Satyanarayana et al., "Steroselective Synthesis of Diacids by the Nickel Cyanide and Phase-Transfer-Catalyzed Carbonylation of Alkynols. Novel Dependency of Product Stereochemistry and Optimum Stirring Speed on the Nature of the Phase-Transfer Agent," *Organometallics* 1991, vol. 10, 804-807.

Saulnier-Blache et al., "A simple and highly sensitive radioenzymatic assay for lysophosphatidic acid quantification," *J. Lipid Res.* 2000, vol. 41, 1947-1951.

Scarpini et al., "Treatment of Alzheimer's Disease: Current Status and New Perspectives," *Lancet Neurol.* Sep. 2003, vol. 2, 539-547.

Scherr et al., "Structural Basis for the Specific Inhibition of Protein Kinase G, a Virulence Factor of *Mycobacterium tuberculosis*," *PNAS* 2007, vol. 104, No. 29, 12151-12156.

Schopfer et al., "Fatty Acid Transduction of Nitric Oxide Signaling. Nitrolinoleic Acid is a Hydrophobically Stabilized Nitric Oxide Donor," *J. Biol. Chem.* May 13, 2005, vol. 280, No. 19, 19289-19297.

(56) References Cited

OTHER PUBLICATIONS

Schopfer et al., "Nitrolinoleic Acid: An endogenous peroxisome proliferator-activated receptor γ ligand," *Proc. Natl. Acad. Sci.* Feb. 15, 2005, vol. 102(7), 2340-2345.

Schopfer et al., "NO-dependent protein nitration: a cell signaling event or an oxidative inflammatory response?" *Trends Biochem. Sci.* 2003, vol. 28, 646-654.

Schopfer et al., "Covalent Peroxisome Proliferator-activated Receptor γ Adduction by Nitro-fatty Acids: Selective ligand activity and anti-diabetic signaling actions," *J. Biol. Chem.* Apr. 16, 2010, vol. 285, No. 16, 12321-12333.

Schopfer et al., "Detection and quantification of protein adduction by electrophilic fatty acids: mitochondrial generation of fatty acid nitroalkene derivatives," *Free Radic. Biol. Med.* 2009, vol. 46, 1250-1259.

Schopfer (Baker) et al., "Red cell membrane and plasma linoleic acid nitration products: Synthesis, clinical identification, and quantitation," *Proc. Natl. Acad. Sci.* Aug. 10, 2004, vol. 101, No. 32, 11577-11582.

Sculptoreanu et al., "Nitro-Oleic Acid Inhibits Firing and Activates TRPV-1 and TRPA1-Mediated Inward Currents in Dorsal Root Ganglion Neurons from Adult Male Rats," *J. Pharm. Expt. Thera.* 2010, vol. 333, No. 3, 883-895.

Serhan et al., "Anti-Inflammatory Actions of Neuroprotectin D1/Protectin D1 and Its Natural Stereoisomers: Assignments of Dihydroxy-Containing Docosatrienes," *J. Immunology* 2006, vol. 176, 1848-1859.

Setiadi et al., "Vitamin E models. Conformational analysis and stereochemistry of tetralin, choman, thiochroman and selenochroman," *J. Molecular Structure (Theochem)* 2002, vol. 594, 161-172.

Shaner et al., "Designing Herbicide Tolerance Based on Metabolic Alteration: the Challenges and the Future," In *Pesticide Biotransformation in Plants and Microorganisms* (Hall, J. et al.); ACS Symposium Series 2000, American Chemical Society; Washington DC.

Sharpless et al., "A Mild Procedure for the Conversion of Epoxides to Allylic Alcohols. The First Organoselenium Reagent," *J. Am. Chem. Soc.* Apr. 18, 1973, vol. 95, No. 8, 2697-2699.

Sieker et al., "Rubredoxin in Crystalline State," *Methods Enzymol.* 1994, vol. 243, 203-216.

Simopoulos et al., "Omega-3 Fatty Acids in Inflammation and Autoimmune Diseases," *J. Amer. College of Nutrition* 2002, vol. 21, No. 6, 495-505.

Smith, "Prostanoid biosynthesis and mechanisms of action," *Am. Physiol. Soc.* 1992, vol. 263, F181- F191.

Snider et al., "Oxidative and Dehydrative Cyclizations of Nitroacetate Esters with Mn(Oac)$_3$," *Tetrahedron*, Sep. 23, 2002, vol. 58, No. 39, 7821-7827.

Söding et al., "HHsenser: Exhaustive Transitive Profile Search Using HMM-HMM Comparison," *Nucleic Acids Res.* 2006, vol. 34, W374-378.

STN Accession No. 2010:548169, 2010. [per STE, not relevant, so not filed—part of Groeger article "Cyclooxygenase-2 . . . . "

Strowig et al., "Combination therapy using metformin or thiazolidinediones and insulin in the treatment of diabetes mellitus," *Diabetes, Obesity, and Metabolism* 2005, vol. 7, 633-641.

Subczynski et al., "Permeability of Nitric Oxide through Lipid Bilayer Membranes," *Free Radic. Res.* 1996, vol. 24, 343-349.

Szekely et al., "A Novel Drug Discovery Concept for Tuberculosis: Inhibition of Bacterial and Host Cell Signaling," *Immun. Letters* 2008, vol. 116, No. 2, 225-231.

Szoka et al., "Comparative Properties and Methods of Preparation of Lipid Vesicles (Liposomes)," *Annu. Rev. Biophys. Bioeng.* 1980, vol. 9, 467-508.

Tang et al., "Nitroalkenes induce rat aortic smooth muscle cell apoptosis via activation of caspase-dependent pathways," *Biochem. Biophys. Res. Commun.* 2010, vol. 397, 239-244.

Thatcher et al., "Nitrates and No Release: Contemporary Aspects in Biological and Medicinal Chemistry," *Free Radic. Biol. Med.* 2004, vol. 37, No. 8, 1122-1143.

Thomas et al., "The biological lifetime of nitric oxide. Implications for the perivascular dynamics of NO and $O_2$," *Proc. Natl. Acad. Sci.* Jan. 2, 2001, vol. 98, No. 1, 355-360.

Tiwari et al., "Key Residues in *Mycobacterium tuberculosis* Protein Kinase G Play a Role in Regulating Kinase Activity and Survival in the Host," *J. Biolol. Chem.* 2009, vol. 284, No. 40, 27467-27479.

Tontonoz et al., "Stimulation of Adipogenesis in Fibroblasts by PPARγ2, a Lipid-Activated Transcription Factor," *Cell* 1994, vol. 79, 1147-1156.

Tontonoz et al., "mPPARγ2: tissue-specific regulator of an adipocyte enhancer," *Genes Dev.* 1994, vol. 8, No. 10, 1224-1234.

Toth, "High-Density Lipoprotein and Cardiovascular Risk," *Circulation* 2004, vol. 109, 1809-1812.

Trostchansky et al., "Nitrated Fatty Acids: Mechanisms of Formation, Chemical Characterization, and Biological Properties," *Free Rad. Biol. Med.* 2008, vol. 44, 1887-1896.

Tsikas et al., "Nitro-fatty Acids Occur in Human Plasma in the Picomolar Range: a Targeted Nitro-lipidomics GC-MS/MS Study," *Lipids* 2009, vol. 44, 855-865.

Tzameli et al., "Regulated Production of a Peroxisome Proliferatory-Activated Receptor-gamma Ligand during an Early Phase of Adipocyte Differentiation in 3T3-L1 Adipocytes," *J. Biol. Chem.* 2004, vol. 279, No. 34, 36093-36102.

Van Beilen et al., "Rubredoxins Involved in Alkane Oxidation," *J. Biolol. Chem.* 2002, vol. 184, No. 6, 1722-1732.

Vasil'Ev et al., "The action of nitrogen dioxide upon erucic acid," *Lomonosova* 1995, vol. 5, 50-58 (English abstract).

Vickers et al., "IGF-1 Treatment Reduces Hyperphagia, Obesity, and Hypertension in Metabolic Disorders Induced by Fetal Programming," *Endocrinol.* Sep. 2001, vol. 142, No. 9, 3964-3973.

Vidwans et al., "Differential Modulation of Prostaglandin H Synthase-2 by Nitric Oxide-Related Species in Intact Cells," *Biochem.* 2001, vol. 40, 11533-11542.

Villacorta et al., "Nitro-linoleic Acid Inhibits Vascular Smooth Muscle Cell Proliferation via the Keap1/Nrf2 Signaling Pathway," *Am. J. Physiol. Heart Circ. Physiol.* Apr. 27, 2007, 1-9.

Villacorta et al., "PPARγ and its ligands: therapeutic implications in cardiovascular disease," *Clin. Sci.* 2009, vol. 116, 205-218.

Villarino et al., "Proteomic Identification of M. Tuberculosis Protein Kinase Substrates: PknB Recruits GarA, a FHA Domain-containing Protein, Through Activation Loop-mediated Interactions," *J. Mol. Bio.* 2005, vol. 350, No. 5, 953-963.

'Virtual Chembook' in www.elmhurst.edu/~chm/vchembook/551fattyacids.html (retrieved Dec. 12, 2012).

Von Knethen et al., "Activation of Peroxisome Proliferator-Activated Receptor γ by Nitric Oxide in Monocytes/Macrophages Down-Regulates p47$^{phox}$ and Attenuates the Respiratory Burst," *J. Immunol.* 2002, vol. 169, 2619-2626.

Walburger et al., "Protein Kinase G from Pathogenic Mycobacteria Promotes Survival Within Macrophages," *Sci.* 2004, vol. 304, 1800-1804.

Wang et al., "Constitutive Activation of Peroxisome Proliferator-activated Receptor-γ Suppresses Pro-inflammatory Adhesion Molecules in Human Vascular Endothelial Cells," *J. Biol. Chem.* 2002, vol. 277, No. 37, 34176-34181.

Wang et al., "Effects of Endogenous PPAR Agonist Nitro-Oleic Acid on Metabolic Syndrome in Obese Zucker Rats," *PPAR Res.* 2010, vol. 2010, 1-7.

Wang et al., "Nitro-oleic acid protects against endotoxin-induced endotoxemia and multiorgan injury in mice," *Am. J. Physiol. Renal Physiol.* 2010, vol. 298, F754-762.

Weber et al., "Fragmentation of Bovine Serum Albumin by Pepsin. 1. The Origin of the Acid Expansion of the Albumin Molecule," *J. Biolo. Chem.* 1964, vol. 239, No. 5, 1415-1423.

Wehenkel et al., "Mycobacterial Ser/Thr Protein Kinases and Phosphatases: Physiological Roles and Therapeutic Potential," *Biochemica et biophysica acta* 2008, vol. 1784, No. 1, 193-202.

Woodcock, "Synthesis of Nitrolipids. All Four Possible Diastereomers of Nitrooleic Acids: (E)- and (Z)-, 9- and 10-Nitro-octadec-9-enoic Acids," *Organic Letters* 2006, vol. 8, No. 18, 3931-3934.

Wright et al., "Fatty acid transduction of nitric oxide signaling: Nitrolinoleic acid potently activates endothelial heme oxygenase 1 expression," *PNAS* Mar. 14, 2006, vol. 103, No. 11, 4299-4304.

(56) References Cited

OTHER PUBLICATIONS

Wright et al., "Human Heme Oxygenase-1 Induction by Nitro-linoleic Acid is Mediated by cyclic AMP, AP-1, and E-box Response Element Interactions," *Biochem. J.* 2009, m. BJ20090339, 1-31.

Xu et al., "Lysophosphatidic Acid as a Potential Biomaker for Ovarian and Other Gynecologic Cancers," *JAMA* 1998, vol. 280, 719-723.

Zhang et al., "Lysophosphatidic Acid Induces Neointima Formation Through PPARgamma Activation," *J. ExMed.* 2004, vol. 199, No. 6, 763-774.

Zhang et al., "Selective disruption of PPARgamma2 impairs the development of adipose tissue and insulin sensitivity," *Proc. Natl. Acad. Sci.* 2004, vol. 101, No. 29, 10703-10708.

Zhang et al., "Nitro-Oleic Acid Inhibits Angiotensin II-Induced Hypertension," *Circ. Res.* 2010, vol. 107, 540-548.

Cha et al., "Peroxisome Proliferator-Activated Receptor α/γDual Agonist Tesaglitazar Attenuates Diabetic Nephropathy in *db/db* Mice," *Diabetes*, vol. 56, pp. 2036-2046, Aug. 2007.

Yamamoto et al., "Identification of putative metabolics of docosahexaenoic acid as potent PPARγ agonists and antidiabetic agents," *Bioorganic & Medicinal Chemistry Letters*, vol. 15, pp. 517-522, Dec. 16, 2004.

\* cited by examiner

NITRATED-FATTY ACIDS MODULATION OF TYPE II DIABETES

CROSS-REFERENCE TO RELATED PATENT APPLICATIONS

This is a Continuation of U.S. patent application Ser. No. 14/244,741, filed Apr. 3, 2014, now U.S. Pat. No. 9,186,408, issued Nov. 17, 2015, which is a Continuation of U.S. patent application Ser. No. 13/666,827, filed Nov. 1, 2012, now U.S. Pat. No. 8,735,449, issued May 27, 2014, which is a Continuation of U.S. patent application Ser. No. 12/670,951, filed May 10, 2010, now U.S. Pat. No. 8,324,277, issued Dec. 4, 2012, which is the U.S. National Stage of International Application No. PCT/US08/09274, filed Aug. 1, 2008, which was published in English under PCT Article 21 (2), which in turn claims the benefit of U.S. Provisional Application No. 60/953,360, filed Aug. 1, 2007, all of which are hereby incorporated by reference.

STATEMENT REGARDING FEDERALLY SPONSORED RESEARCH

This invention was made with United States government support under grant number R01 HL58115, awarded by the National Institutes of Health. The United States government has certain rights in the invention.

BACKGROUND OF THE INVENTION

The present invention relates to the use of nitrated fatty acids as therapeutics for treating type-2 diabetes. Fatty acids are both physiological energy sources and mediators of signaling events involved, for example, in inflammation and in energy homeostasis.

Saturated, unsaturated, and polyunsaturated fatty acids have been identified to date. Unsaturated electrophilic fatty acids have emerged as an important class of endogenous signaling molecules. Within this class are fatty acid hydroperoxides, keto fatty acids, and nitrated fatty acids, among others. For example, see Freeman et al., *Chem. Res. Toxicol.* 12: 83-92 (1999), and Lima et al., *Biochemistry* 41: 10717-22 (2002).

The signaling ability of nitro fatty acids stems predominantly from their ability to form reversible covalent adducts with nucleophilic centers of cellular proteins that are implicated in various transcriptional and cellular signaling processes. In particular, regulation of signaling activity most often occurs via the covalent modification of an active site thiol group of a protein target.

Recent studies suggest that nitro fatty acids such as 9- or 10-nitro octadecenoic acid ("nitro oleic acid") and the various regioisomers (9-, 10-, 12- and 13-nitro) of nitro linoleic acid are adaptive mediators that play a crucial role in linking disease processes with underlying cellular events. See Freeman et al., *Proc. Nat'l Acad. Sci. USA* 99: 15941-46 (2002). In particular, nitro fatty acids modulate the activity of the peroxisome proliferator activating receptor gamma (PPAR-γ), for example, in response to inflammation and metabolic imbalance.

While both nitro oleic acid and nitro linoleic acid interact with PPAR-γ, little is known about the structural and biochemical determinants that account for their PPAR-γ activity and the related downstream activation of gene transcription. Consequently, no systematic approach exits for the design of pharmacophores that can modulate PPAR-γ activity.

SUMMARY OF THE INVENTION

Accordingly, the present invention provides, in one of its aspects, a pharmaceutical composition comprising (A) an active agent selected from nitro oleic acid and a metabolite of nitro oleic acid, or a pharmaceutically acceptable salt or prodrug of such active agent, and (B) a pharmaceutically acceptable carrier. In a preferred embodiment, the active agent is nitro oleic acid.

In accordance with another of its aspects, the invention provides a method for treating type-2 diabetes, comprising (A) administering to a subject in need thereof a pharmaceutical composition as described above and then (B) repeating step (A) at least once. Preferably, the method further comprises, after at least one repetition of step (A); the monitoring of the subject for a change relating to type-2 diabetes.

Pursuant to yet another aspect of the invention, a method is provided for gauging efficacy of a treatment for type-2 diabetes. This method comprises (A) obtaining a first and a second sample from a subject suffering from type-2 diabetes, which samples are obtained at different times during said treatment; (B) determining blood glucose levels in the first and second samples; and (C) comparing the blood glucose level between the samples. In accordance with these steps, a lower blood glucose level in the second sample is an indicator of efficacy of the treatment.

DETAILED DESCRIPTION OF THE INVENTION

Nitro oleic acid and related metabolic products ("metabolites") are agonists of PPAR-γ. The inventor's discovery that nitro oleic acid is surprisingly more potent as an agonist of PPAR-γ, relative to nitro linoleic acid, underscores the prospect, in accordance with the present invention, of using nitro oleic acid and its metabolites, as well as their pharmaceutically acceptable salts and prodrug forms, as active agents in the treatment of type-2 diabetes, which results from insulin resistance accompanying the improper functioning of PPAR-γ.

The structural determinants responsible for the potency of nitro oleic acid and its metabolites at PPAR-γ were illuminated using a computational model for receptor-ligand interaction. Modeling data indicate that both arginine-288

(Arg288) and cysteine-285 (Cys285), present in the ligand binding pocket of PPAR-γ, are important for binding. For example, the receptor-ligand model indicates an electrostatic interaction between arginine-288 and the anionic nitro group of nitro oleic acid, while Cys285 is found to be in a suitable position for interacting with the olefinic double bond. These observations indicate that nitro oleic acid activates PPAR-γ via the covalent modification of its active site thiol, and compounds that preserve such interactions will activate the receptor in a similar manner, thus qualifying as a candidate therapeutic for treating type-2 diabetes.

Figure 1:
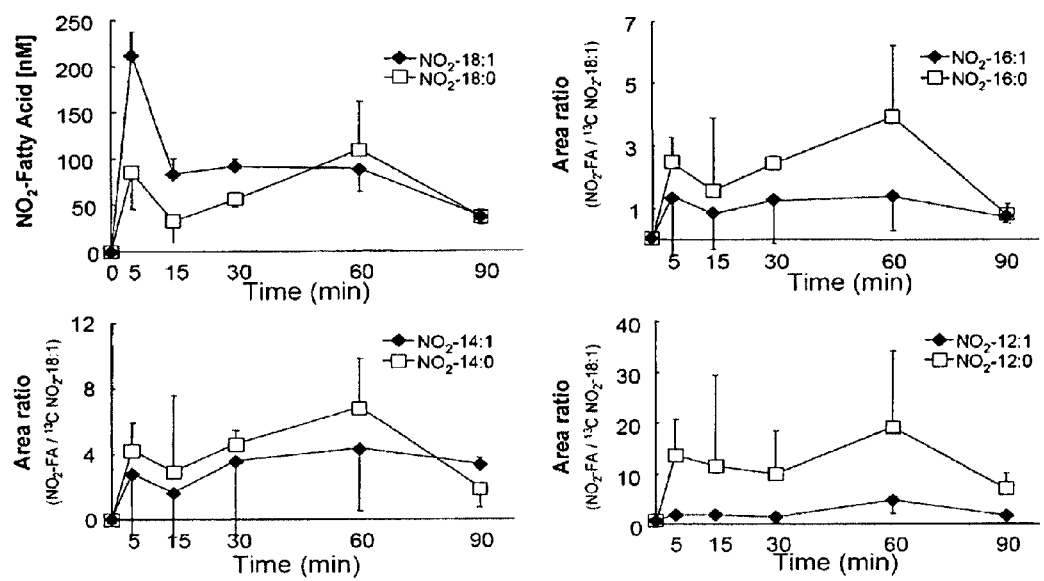
FIG. 1 is a graph depicting serum levels of nitro oleic acid and as its physiological metabolites as a function of time.

Analysis of mouse plasma after intravenous administration of nitro oleic acid illuminates the physiological fate of nitro oleic acid. Nitro oleic acid is converted in-vivo, to its saturated analog, or can undergo β-oxidative cleavage to give several short chain products, such as the corresponding saturated or unsaturated C-10 to C-16 nitrated analogs. FIG. 1 shows the plasma levels of nitro oleic acid or its metabolic products as a function of time. For nitro oleic acid as well as its saturated 18:0 nitrated analog, the curve is biphasic, with peak concentrations occurring at around 5 minutes following the administration of nitro oleic acid. In contrast, the plasma levels for the β-oxidation products are highest at around 60 minutes.

The presence of β-oxidation products in blood plasma has important physiological implications. It is believed that the short-chain metabolites are less hydrophobic than the parent acid. Nevertheless, these compounds preserve the molecular determinants that are believed to be important for binding. Additionally, the smaller size the C-10 to C-16 metabolic products will allow these metabolites to partition differently between the hydrophobic and hydrophilic compartments physiologically. Such differences in partitioning ratios alter the anatomic distribution, chemical reactivity, and pharmacological profiles of these metabolites, by altering their availability to cellular targets. Pursuant to the invention, the C-10 to C-16 metabolites are also suitable candidate therapeutics for the treatment of type-2 diabetes, a condition associated with PPAR-γ dysfunction. See Freeman et al., *Chem. Res. Toxicol.* 12: 83-92 (1999).

Supportive of this anti-diabetic indication, nitro oleic acid was found to improve insulin sensitivity and lower blood glucose levels in ob/ob mice. In particular, in-vivo results indicate that nitro oleic acid reduces blood glucose levels without the side-effects of weight gain and fluid retention associated with Rosiglitazone, a known PPAR-γ agonist.

Figure 2:
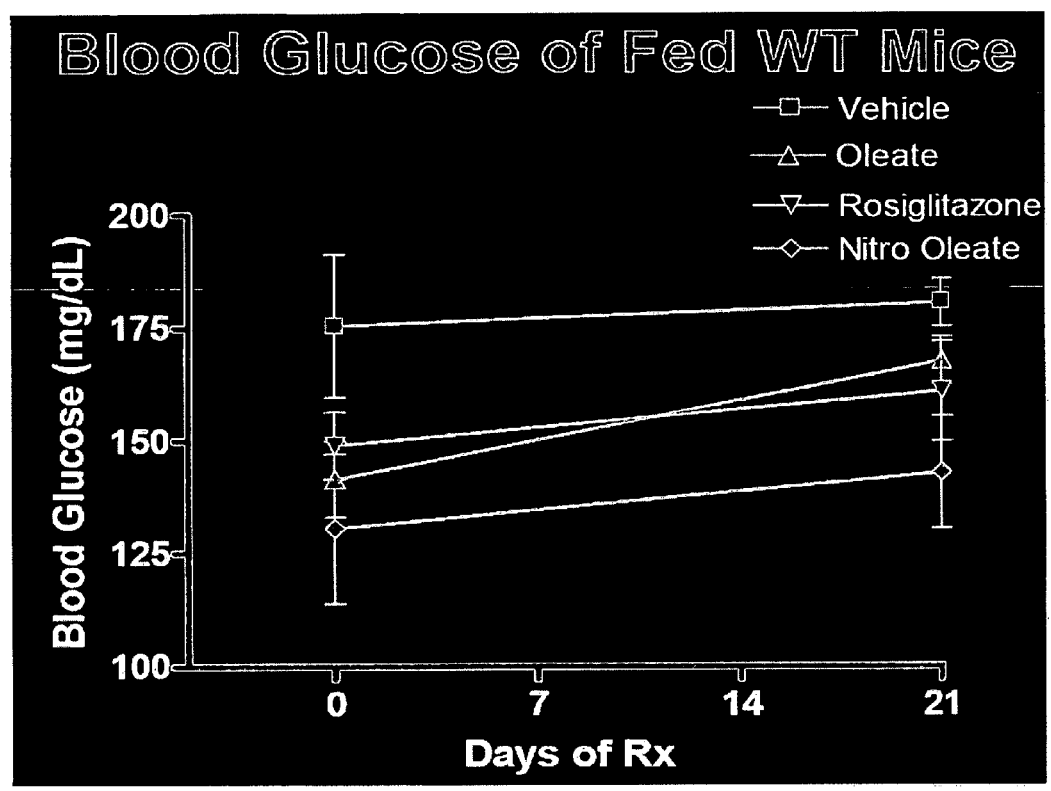
FIG. 2 is a graph that correlates blood glucose levels in wild-type (WT) mice on different days after injection with oleic acid, nitro oleic acid, rosiglitazone, and a vehicle.

As shown in FIG. 2, nitro oleic acid but not oleic acid maintains a steady blood glucose level in fed WT mice. The in-vivo results indicate that nitro oleic acid was at least as effective as Rosiglitazone in maintaining blood glucose levels. Similar results are observed in experiments involving ob/ob mice. As seen from the graph in FIG. 3, both nitro oleic acid and Rosilitazone are effective in reducing blood glucose levels. However, for mice receiving oleic acid the blood glucose levels increased over the course of the study. These results, therefore, provide support for nitro oleic acid's role in lowering blood glucose and as a candidate therapeutic for the treatment of diabetes.

Figure 4:
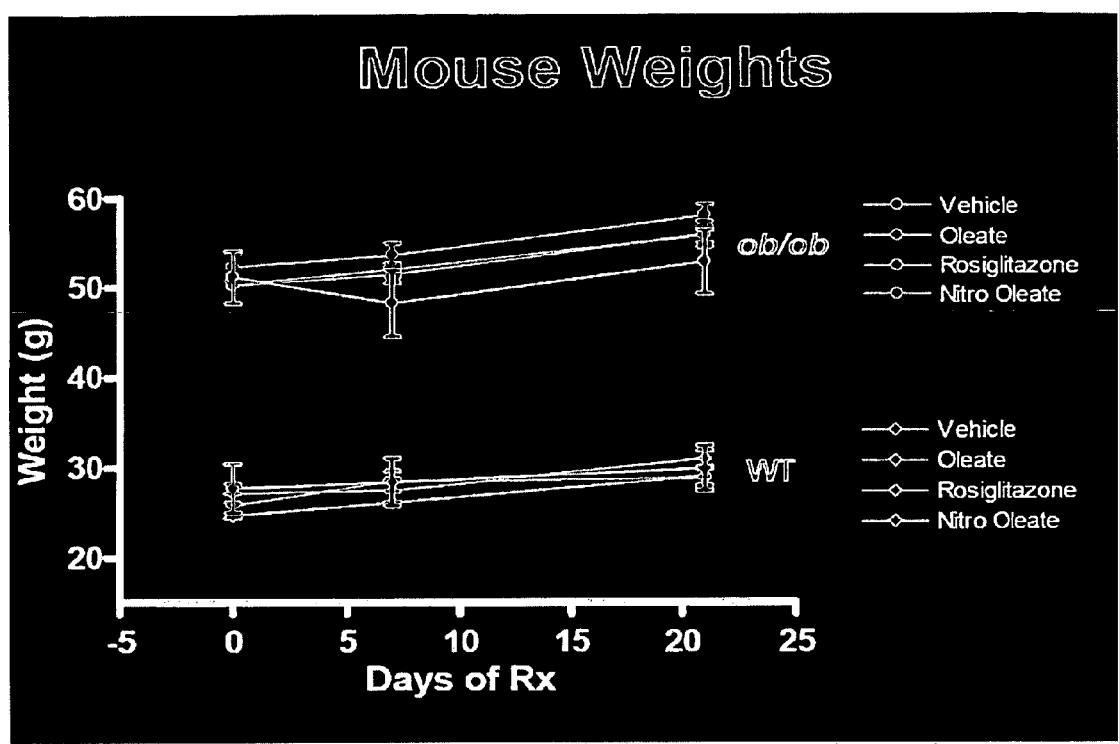
FIG. 4 is a graph that correlates the body weights of WT and ob/ob mice, undergoing treatment with nitro oleic acid, to the body weight of WT and ob/ob mice that receive oleic acid, rosiglitazone, and a vehicle, respectively.

In addition to reducing blood glucose levels, no increase in body weight is observed when nitro oleic acid is administered to mice. As shown in FIG. 4, the body weights of WT mice receiving nitro oleic acid, or Rosiglitazone do not change over the course of the study (25 days), however, the results are substantially different for ob/ob mice. In this case, the body weight initially decreases for animals receiving nitro oleic acid (days 0-10) and then remains constant over the latter half of the study. In contrast, animals receiving Rosilitazone or oleic acid show a steady increase in body weights over the entire course of the study.

Without endorsement of any particular theory, the absence of weight gain in ob/ob mice is believed to occur because physiologically nitro oleic acid is adduced to plasma, which serves as a "storage system" and temporarily inactivates the nitrated fatty acid, until it is required for facilitating a particular signal transduction event. Since activation of PPAR-γ occurs upon binding free nitro oleic acid, the sequestration of this molecule prevents the aberrant activation of PPAR-γ or the transcription of genes that are regulated by this nuclear receptor.

Figure 5:
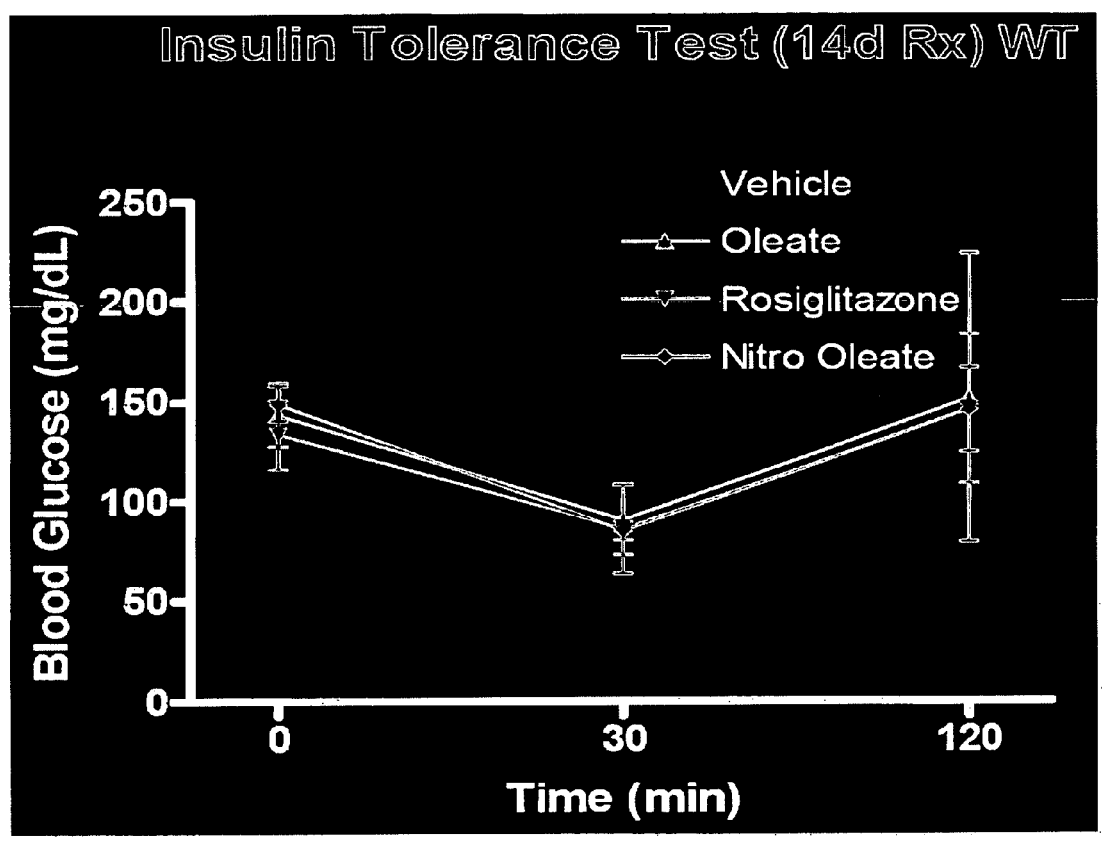
FIG. 5 is a graph that shows the change in insulin sensitivity for WT mice injected with oleic acid, nitro oleic acid, rosiglitazone, and a vehicle, respectively
Figure 6:
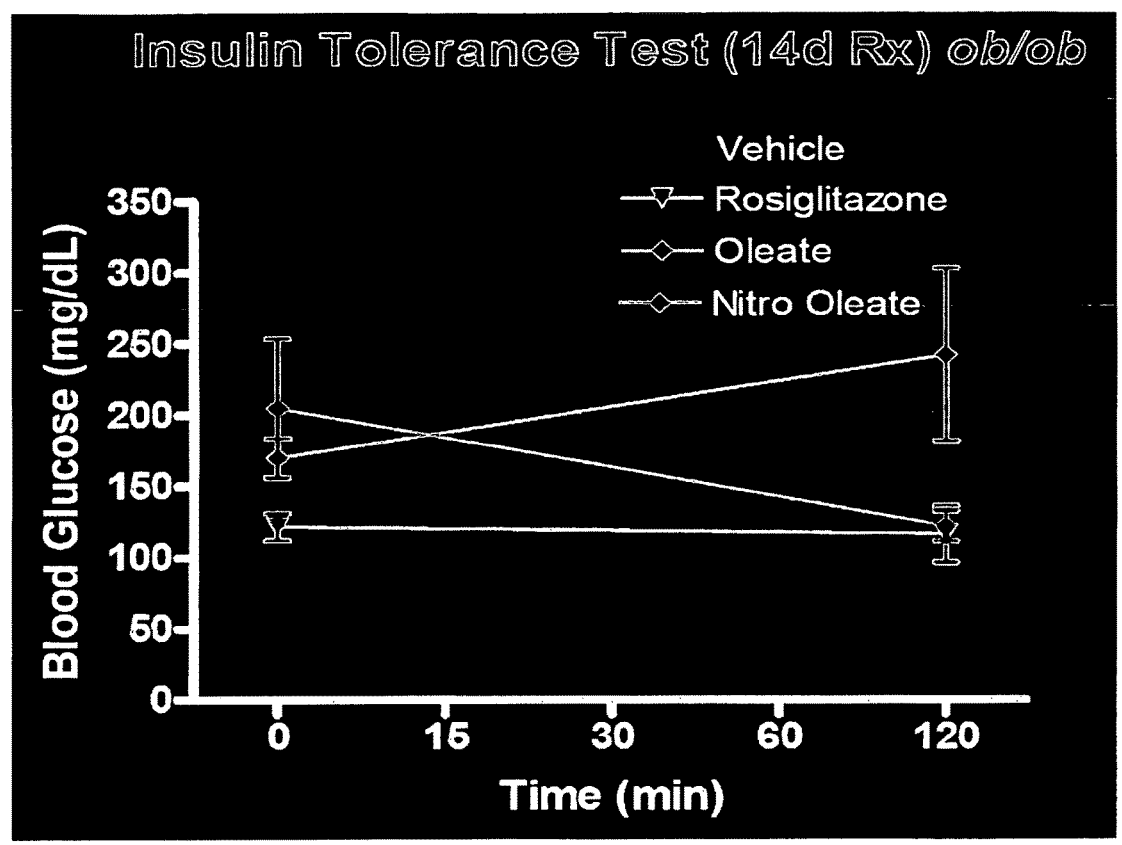
FIG. 6 is a graph that documents a change in insulin sensitivity of ob/ob mice, observed after injection with oleic acid, nitro oleic acid, rosiglitazone, and a vehicle, respectively.

Further evidence, that nitro oleic acid modulates PPAR-γ activity via a binding interaction different from that of Rosiglitazone is provided by the discovery that nitro oleic acid and not Rosiglitazone improves insulin sensitivity in ob/ob mice. In this regard, for WT mice receiving either nitro oleic acid or Rosiglitazone, the administration of insulin results in an initial drop in blood glucose levels followed by an elevation to normal levels shortly after the administration of insulin as shown in FIG. 5. In contrast, as seen by the graph in FIG. 6, administration of nitro oleic acid to ob/ob mice followed by the administration of insulin causes a substantial decrease in blood glucose levels. On the other hand, the blood glucose levels in ob/ob mice receiving Rosiglitazone are unchanged upon administration of insulin. These results indicate that administration of nitro oleic prior to insulin enhances insulin sensitivity in ob/ob diabetic mice, while Rosiglitazone fails to do so. The fact that both nitro oleic acid and Rosiglitazone exert their blood glucose lowering effect through the activation of PPAR-γ, indicates that they interact differently with the receptor and consequently the transcription of genes that regulate metabolic events that lead to weight gain and fluid retention.

The importance of nitro fatty acids as signaling molecules has prompted the development of various procedures for synthesizing these compounds. For example, Brandchaud et al., *Org. Lett.* 8: 3931-34 (2006), and King et al., *Org. Lett.* 8: 2305-08 (2006), disclose syntheses that could be used in the context of the present invention. Another suitable synthesis approach, disclosed in U.S. Patent Publication No. 2007/0232579, involves the direct nitration of an appropriate unsaturated fatty acid. Accordingly, (Z)-octadec-9-enoic acid (oleic acid) is reacted with $NaNO_2$ in the presence of phenylselenium bromide and mercuric chloride under anhydrous conditions to give 9-nitro or 10-nitro oleic acid. A similar synthetic strategy is believed to nitrate the appropriate C-10 to C-16 unsaturated fatty acids to give the corresponding nitro oleic acid metabolic products.

Thus obtained, the synthetic regioisomers of nitro oleic acid or their respective C-10 to C-16 metabolites are typically purified prior to biological use. In one aspect of the invention, therefore, large-scale purification of the individual isomers is carried out using preparative high performance liquid chromatography (HPLC), as described in U.S. Patent Publication No. 2007/0232579. The purified compounds thus obtained are appropriately formulated prior to in vivo administration.

A pharmaceutical composition of the invention can include one or more therapeutic agents in addition to nitro oleic acid or a related compound, as described above. Illustrative of such therapeutics are cytokines, chemokines, and/or regulators of growth factors. Additionally, the invention contemplates a formulation that contains either a single regioisomer or both regioisomers of nitro oleic acid.

The pharmaceutical composition can have more than one physiologically acceptable carrier, too, such as a mixture of two or more carriers. The composition also can include thickeners, diluents, solvents, buffers, preservatives, surface active agents, excipients, and the like.

The pharmaceutical carrier used to formulate the nitro oleic acid of the invention will depend on the route of administration. Administration may be topical (including opthamalic, vaginal, rectal, or intranasal), oral, by inhalation, or parenterally, for example by intravenous drip, subcutaneous, intraperitoneal or intramuscular injection.

Thus, nitro oleic acid or its metabolites can be administered intravenously, intraperitoneally, intramuscularly, subcutaneously, intracavity, transdermally, intratracheally, extracorporeally, or topically (e.g., topical intranasal administration or administration by inhalant). In this regard, the phrase "topical intranasal administration" connotes delivery of the compositions into the nose and nasal passages through one or both of the nares and can comprise delivery by a spraying mechanism or droplet mechanism, or through aerosolization of the nucleic acid or vector. The latter can be effective when a large number of subjects are to be treated simultaneously, where "subject" can denote a human or an non-human animal. Administration of the compositions by inhalant can be through the nose or mouth via delivery by a spray or droplet mechanism. Delivery also can be directed to any area of the respiratory system, such as the lungs, via intubation.

A pharmaceutical composition of the nitro oleic acid and its metabolites for parenteral administration, according to the invention, can include excipients and carriers that stabilize the nitro fatty acid mimetic. Illustrative of such a carrier are non-aqueous solvents, such as propylene glycol, polyethylene glycol, vegetable oils, and injectable organic esters such as ethyl oleate. Additionally, formulations for parenteral administration include liquid solutions, suspensions, or solid forms suitable for solution or suspension in liquid prior to injection, or emulsions.

Intravenous compositions can include agents to maintain the osmomolarity of the formulation. Examples of such agents include sodium chloride solution, Ringer's dextrose, dextrose, lactated Ringer's solution, fluid and nutrient replenishers, and the like. Also included in intravenous formulations are one or more additional ingredients that prevent microbial infection or inflammation, as well as anesthetics.

Alternatively, pharmaceutical compositions of the salt form of nitro oleic acid or its metabolites is administered. Illustrative of such salts are those formed by reaction of the carboxyl group with an inorganic base such as sodium hydroxide, ammonium hydroxide, or potassium hydroxide. Additionally, the salt is formed by reacting the carboxyl group with organic bases such as mono-, di-, trialkyl and aryl amines and substituted ethanolamines.

To address concerns that at physiological pH, nitro oleic acid typically will be a negatively charged molecule, which may have non-optimal bioavailability and cell-transport kinetics, one may provide a compound of the invention formulated as a prodrug. Illustrative of such a prodrug is a pharmaceutically acceptable ester, such as a methyl or an ethyl ester. The ester acts as a prodrug because non-specific intracellular esterase convert it to the active form responsible for eliciting therapeutic effect.

Type-2 diabetes is a chronic condition that results from a loss of sensitivity to insulin. As described above, a pharmaceutical composition of the invention improves insulin sensitivity and, hence, can serve as a therapeutic for treating type-2 diabetes. Successful treatment of type-2 diabetes typically entails as well an ongoing monitoring of the subject for changes related to the diabetic condition, e.g., monitoring physiological levels of different metabolic parameters associated with this condition. Thus, the subject's blood and urine glucose levels can be measured to assess how frequently to administer the inventive composition. Additional markers such as a gain in body weight, frequency of urination and the levels of glucagon in the blood can be used to monitor and possibly to modify treatment to best suit the given subject.

In support of such an anti-diabetic regimen, the present invention also provides for using one of the above-mentioned active agents to prepare a pharmaceutical composition for treating type-2 diabetes in a subject. To this end, different formulation approaches have been described above.

Figure 3:
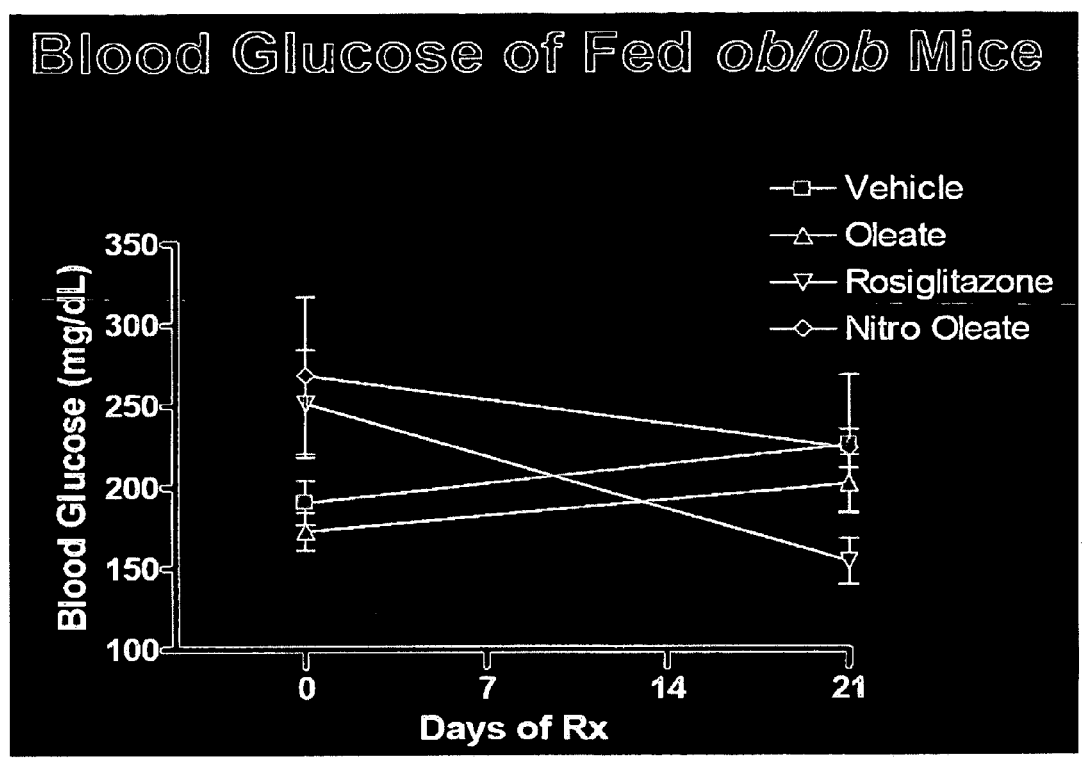
FIG. 3 is a graph that correlates blood glucose levels in leptin-deficient diabetic ob/ob mice on different days after being injected with oleic acid, nitro oleic acid, rosiglitazone, and a vehicle.

In a related vein, the invention encompasses a method for gauging the therapeutic efficacy of the composition as described above. This method involves obtaining at least two blood samples from a subject at different times during treatment and measuring the level of blood glucose in each sample. Indicative of therapeutic efficacy is a lower level of blood glucose in the sample obtained at a later time point during treatment. As shown in FIG. 3, blood glucose levels in ob/ob mice receiving nitro oleic acid are significantly lower on day 21 than at the beginning of the study, indicating the therapeutic benefit of nitro oleic acid in treatment of type 2 diabetes.

What is claimed is:

1. A method for lowering blood glucose levels, comprising administering a nitro oleic acid, or a metabolite, a pharmaceutically acceptable salt, or prodrug thereof to a subject in need of treatment.

2. The method of claim 1, wherein administering is carried out by a method selected from the group consisting of topical administration, oral administration, inhalation, intravenous drip, subcutaneous injection, intraperitoneal injection, and intramuscular injection.

3. The method of claim 1, further comprising administering one or more therapeutic agents in addition to the nitro oleic acid.

4. The method of claim 3, wherein the one or more therapeutic agents are selected from the group consisting of cytokines, chemokines, and regulators of growth factors.

5. The method of claim 1, wherein the subject is a human.

6. The method of claim 1, further comprising administering an anti-microbial agent, an anti-inflammation agent, an anesthetic, or a combination thereof.

7. The method of claim 1, wherein the nitro oleic acid is a salt of an inorganic base selected from the group consisting of sodium hydroxide, ammonium hydroxide, potassium hydroxide, monoalkyl amine, dialkyl amine, trialkyl amine, aryl amine, substituted ethanolamine, and a combination thereof.

8. The method of claim 1, wherein the nitro oleic acid is a prodrug selected from the group consisting of a methyl ester of nitro oleic acid or an ethyl ester of nitro oleic acid.

9. The method of claim 1, wherein the nitro oleic acid, metabolite, salt, or prodrug thereof is in a pharmaceutical composition.

10. The method of claim 9, wherein the pharmaceutical composition further comprises sodium chloride, Ringer's dextrose, dextrose, lactated Ringer's solution, fluid and nutrient replenishers, or a combination thereof.

11. The method of claim 9, wherein the pharmaceutical composition is a solution, suspension, solid, or emulsion.

12. The method of claim 9, wherein the pharmaceutical composition further comprises thickeners, diluents, solvents, buffers, preservatives, surface active agents, excipients, or a combination thereof.

* * * * *